United States Patent [19]
Ziegler et al.

[11] Patent Number: 5,932,583
[45] Date of Patent: Aug. 3, 1999

[54] TRIAZOLINE AND ISOXAZOLINE BIS-OXIME DERIVATIVES AND THEIR USE AS PESTICIDES

[75] Inventors: Hugo Ziegler, Witterswil, Switzerland; Stephan Trah, Freiburg, Germany; René Zurflüh; Anthony Cornelius O'Sullivan, both of Basel, Switzerland

[73] Assignee: Novartis Crop Protection, Inc., Greensboro, N.C.

[21] Appl. No.: 08/981,116

[22] PCT Filed: Jun. 21, 1996

[86] PCT No.: PCT/EP96/02695

§ 371 Date: Dec. 23, 1997

§ 102(e) Date: Dec. 23, 1997

[87] PCT Pub. No.: WO97/02255

PCT Pub. Date: Jan. 23, 1997

[30] Foreign Application Priority Data

Jul. 4, 1995 [CH] Switzerland ............................ 1949/95
May 24, 1996 [CH] Switzerland ............................ 1319/96

[51] Int. Cl.$^6$ .......................... A61K 31/41; A61K 31/42; C07C 249/08; C07C 251/52; C07D 249/12; C07D 261/12

[52] U.S. Cl. .......................... 514/256; 514/357; 514/380; 514/384; 514/524; 514/533; 514/534; 514/538; 544/333; 546/272.1; 546/272.4; 548/243; 548/263.2; 548/264.6; 558/13; 560/35; 564/265

[58] Field of Search .......................... 544/333; 546/272.1, 546/272.4; 548/243, 263.2, 264.6; 514/256, 357, 380, 384

[56] References Cited

FOREIGN PATENT DOCUMENTS

| 90 07493 | 7/1990 | WIPO | ............................ C07C 251/60 |
|---|---|---|---|
| 95 14009 | 5/1995 | WIPO | ............................ C07D 249/12 |
| 95 18789 | 7/1995 | WIPO | ............................ C07C 251/60 |
| 95 21153 | 8/1995 | WIPO | ............................ C07C 251/34 |
| 96 36229 | 11/1996 | WIPO | ............................ A01N 43/653 |
| 96 36616 | 11/1996 | WIPO | ............................ C07D 249/12 |

*Primary Examiner*—Johann Richter
*Assistant Examiner*—Jane C. Osweki
*Attorney, Agent, or Firm*—Michael P. Morris; William A. Teoli, Jr.; John D. Peabody, III

[57] ABSTRACT

Bis-oxime derivatives of the formula I

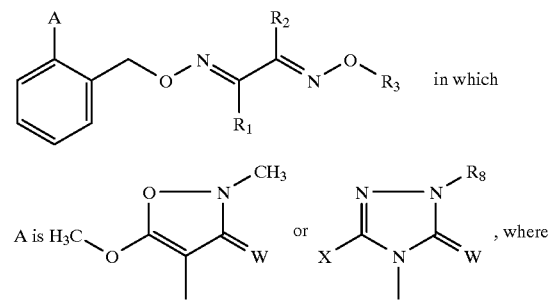

in which

W is oxygen or sulfur, and the other substituents defined as follows:

$R_1$=hydrogen, $C_1-C_4$alkyl; cyclopropyl;

$R_2$=hydrogen, $C_1-C_6$alkyl; halo($C_1-C_6$) alkyl; $C_2-C_6$alkoxyalkyl; $C_3-C_6$cycloalkyl; substituted or unsubstituted aryl; substituted or unsubstituted heteroaryl; cyano; $C_1-C_6$alkoxycarbonyl; $C_1-C_6$alkyl-S(O)$_n$; substituted or unsubstituted aryl-S(O)$_n$; $C_1-C_6$alkoxy; substituted or unsubstituted aryloxy; substituted or unsubstituted heteroaryloxy; unsubstituted or mono- to trimethyl-substituted heterocyclyl; substituted or unsubstituted aryl-$C_1-C_6$alkyl; substituted or unsubstituted heteroaryl-$C_1-C_6$alkyl;

$R_3$=hydrogen; $C_1-C_6$alkyl; $C_1-C_6$haloalkyl having 1 to 5 halogen atoms; $C_1-C_4$alkoxy-$C_1-C_2$-alkyl; unsubstituted or mono- to trihalo-substituted $C_1-C_6$alkenyl; $C_2-C_6$alkynyl; unsubstituted or mono- to tetrahalo-substituted $C_3-C_6$cycloalkyl-$C_1-C_4$alkyl;

n=0 to 2;

$R_8$=H, $C_1-C_4$alkyl, $C_1-C_4$haloalkyl, $C_3-C_6$cycloalkyl;

X=OR$_5$, SR$_5$, NR$_6$R$_7$, halogen (especially Cl);

$R_6$, $R_7$=independently of one another H, $C_1-C_4$alkyl, $C_3-C_4$alkenyl, $C_3-C_4$alkynyl;

$R_5$=$C_1-C_4$alkyl, $C_1-C_3$haloalkyl, are fungicidal, acaricidal and insecticidal active ingredients for agriculture. They can be employed as formulated crop protection compositions.

18 Claims, No Drawings

TRIAZOLINE AND ISOXAZOLINE BIS-OXIME DERIVATIVES AND THEIR USE AS PESTICIDES

This application is a 371 of PCT/EP96/02695 filed Jun. 21, 1996.

The present invention relates to novel bis-oxime derivatives of the formula I having a microbicidal, insecticidal and acaricidal action,

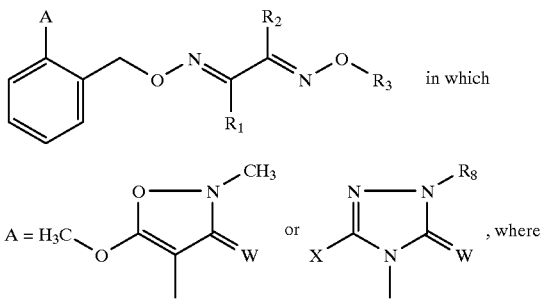 in which

W is oxygen or sulfur, and the other substituents are defined as follows:

$R_1$=hydrogen, $C_1$–$C_4$alkyl; cyclopropyl;

$R_2$=hydrogen, $C_1$–$C_6$alkyl; halo($C_1$–$C_6$)alkyl; $C_2$–$C_6$alkoxyalkyl; $C_3$–$C_6$cycloalkyl; substituted or unsubstituted aryl; substituted or unsubstituted heteroaryl; cyano; $C_1$–$C_6$alkoxycarbonyl; $C_1$–$C_6$alkyl-S(O)$_n$; substituted or unsubstituted aryl-S(O)$_n$; $C_1$–$C_6$alkoxy; substituted or unsubstituted aryloxy; substituted or unsubstituted heteroaryloxy; unsubstituted or mono- to trimethyl-substituted heterocyclyl; substituted or unsubstituted aryl-$C_1$–$C_6$alkyl; substituted or unsubstituted heteroaryl-$C_1$–$C_6$alkyl;

$R_3$=hydrogen; $C_1$–$C_6$alkyl; $C_1$–$C_6$haloalkyl having 1 to 5 halogen atoms; $C_1$–$C_4$alkoxy-$C_1$–$C_2$-alkyl; unsubstituted or mono- to trihalo-substituted $C_1$–$C_6$alkenyl; $C_2$–$C_6$alkynyl; unsubstituted or mono- to tetrahalo-substituted $C_3$–$C_6$cycloalkyl-$C_1$–$C_4$alkyl;

n=0 to 2;

$R_8$=H, $C_1$–$C_4$alkyl, $C_1$–$C_4$haloalkyl, $C_3$–$C_6$cycloalkyl;

X=OR$_5$, SR$_5$, NR$_6$R$_7$, halogen (especially Cl);

$R_6$, $R_7$=independently of one another H, $C_1$–$C_4$alkyl, $C_3$–$C_4$alkenyl, $C_3$–$C_4$alkynyl;

$R_5$=$C_1$–$C_4$alkyl, $C_1$–$C_3$haloalkyl.

In a narrower sense, and as a particularly important subgroup, the invention relates to compounds of the formula I in which A is the structural element

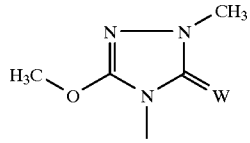

in which W is oxygen or sulfur, $R_2$ is as defined with the exception of halo-($C_1$–$C_6$)alkyl, and $R_1$, $R_3$ and n are as defined above.

Substituents of the optionally substituted aryl, heteroaryl, aryl-S(O)$_n$, aryloxy, heteroaryloxy, aryl-$C_1$–$C_6$alkyl and heteroaryl-$C_1$–$C_6$alkyl groups include $C_1$–$C_4$alkyl, $C_1$–$C_6$alkoxy, $C_1$–$C_4$haloalkyl, $C_1$–$C_4$haloalkoxy, $C_1$–$C_4$alkylthio, $C_1$–$C_4$alkylsulfinyl, $C_1$–$C_4$alkylsulfonyl, halogen, nitro, cyano, substituted or unsubstituted aryl, substituted or unsubstituted aryloxy, substituted or unsubstituted arylthio, substituted or unsubstituted heteroaryl, substituted or unsubstituted heteroaryloxy, substituted or unsubstituted heteroarylthio, unsubstituted, mono- or dihalo-substituted and/or mono- or dimethyl-substituted cyclopropylmethoxy, substituted or unsubstituted $C_2$–$C_6$alkynyl, unsubstituted or mono- to trihalo-substituted $C_2$–$C_6$alkenyl and unsubstituted or substituted benzyloxy.

Suitable substituents for the latter aryl and heteroaryl groups are halogen, $C_1$–$C_4$alkyl, $C_1$–$C_4$alkoxy, $C_1$–$C_4$haloalkyl (e.g. $CF_3$) and $C_1$–$C_4$haloalkoxy (e.g. —$OCF_3$).

Suitable substituents for a substituted or unsubstituted $C_2$–$C_6$alkynyl group located on $R_2$=aryl (especially phenyl) are: $C_1$–$C_4$alkyl, $C_1$–$C_4$alkoxy, $C_1$–$C_4$haloalkyl (e.g. $CF_3$), $C_1$–$C_4$haloalkoxy (e.g. $OCF_3$), $C_1$–$C_4$alkylthio, $C_1$–$C_4$alkylsulfinyl, $C_1$–$C_4$alkylsulfonyl, halogen, nitro, cyano, substituted or unsubstituted phenyl, pyridoyl or benzoyl (the substituents on these six-membered rings possibly being $C_1$–$C_4$alkyl, $C_1$–$C_4$alkoxy, $C_1$–$C_4$haloalkyl [especially $CF_3$], $C_1$–$C_4$haloalkoxy [especially $OCF_3$], $C_1$–$C_4$alkylthio, halogen, nitro, cyano, $C_1$–$C_4$alkylsulfinyl, $C_1$–$C_4$alkylsulfonyl), and also unsubstituted or $C_1$–$C_4$acylated or O—$C_1$–$C_4$alkylated $C_1$–$C_4$hydroxyalkyl, $C_1$–$C_5$alkoxycarbonyl; N,N-di($C_1$–$C_4$alkyl)carbamoyl; N—$C_1$–$C_4$alkyl-N—$C_1$–$C_4$alkoxycarbamoyl; unsubstituted or halo-substituted cyclopropyloxycarbonyl or $C_2$–$C_5$alkenyl, which is unsubstituted or substituted by $C_2$–$C_4$alkoxy and/or halogen; and also five- or six-membered heteroaryl with one or more heteroatoms N, O, S, which can be unsubstituted or substituted by one or more of the substituents halogen, cyano, hydroxyl and also alkyl, alkenyl, alkoxy, alkenyloxy, alkynyloxy having in each case up to 4 carbon atoms.

Each substituent may independently of the others be present 1 to 3 times.

An important subgroup of active substances in this respect are those in which:

$R_1$ is hydrogen, methyl, ethyl or cyclopropyl;

$R_2$ is a phenyl group carrying an unsubstituted or substituted ethynyl group whose possible substituents are: $C_1$–$C_4$alkyl (e.g. methyl, ethyl), $C_1$–$C_4$hydroxyalkyl, halogen, $C_1$–$C_4$haloalkyl, cyano, $C_1$–$C_5$alkoxycarbonyl, cyclopropylmethoxycarbonyl; $C_2$–$C_5$alkenyl which is unsubstituted or substituted by $C_2$–$C_4$alkoxy and/or halogen; N-methyl-N-methoxycarbamoyl; unsubstituted or substituted phenyl (where the substituents are selected from the group consisting of $C_1$–$C_4$alkyl, $C_1$–$C_4$alkoxy, $CF_3$, CN, halogen (e.g. chlorine) and $OCF_3$); unsubstituted or substituted five- to six-membered heteroaryl [e.g. pyridyl, pyrazinyl, pyrimidinyl, thienyl, (iso)thiazolyl] (where the substituents can be halogen, cyano, methyl, methoxy or hydroxyl); and $R_3$ is methyl, ethyl or allyl.

As a further important subgroup, the invention relates to compounds of the formula I in which $R_1$ is hydrogen, methyl, ethyl or cyclopropyl, $R_2$ is hydrogen, methyl, ethyl, cyclopropyl, cyano, methoxycarbonyl, —S(O)$_n$$C_1$–$C_4$alkyl or $C_1$–$C_5$alkoxy, or is a naphthyl, biphenyl, phenoxyphenyl or phenylthiophenyl ring system each of which can be unsubstituted or substituted by from one to three substituents selected from the group consisting of halogen and $C_1$–$C_2$alkyl;

or is a phenyl radical attached directly or via oxygen, $S(O)_n$, or $CH_2$, which is unsubstituted or is substituted by not more than three substituents selected from the group consisting of $C_1$–$C_4$alkyl, $C_1$–$C_4$alkoxy, cyano, halogen, $CF_3$, $OCF_3$, $C_2$–$C_4$alkynyl, $NO_2$, —$S(O)_n$— $C_1$–$C_4$alkyl and a cyclopropylmethoxy group which is unsubstituted or substituted in the ring by one or two halogen atoms;

or is a pyridine or pyrimidine ring which is attached directly or via oxygen or $CH_2$;

or is a thiazoline or oxazoline ring which is unsubstituted or is mono- or disubstituted, identically or differently, by methyl or halogen;

while $R_3$ and n are as defined for formula I.

An important subgroup of the latter compounds are those in which $R_1$ and $R_3$ are methyl and $R_2$ is methyl, cyano, pyridine or is phenyl attached directly or via oxygen, $S(O)_n$ or $CH_2$, which is unsubstituted or substituted by not more than three substituents selected from the group consisting of methyl, methylthio, methoxy, fluorine, chlorine, bromine, $CF_3$, $OCF_3$, propyn-2-yl, $NO_2$ and cyano; or is a thiazole ring or a naphthyl, biphenyl or phenoxyphenyl ring system which is unsubstituted or is substituted in each case up to twice, identically or differently, by methyl and/or halogen; while A and n are as defined for formula I.

A particularly important group comprises those compounds of the formula I in which $R_1$, $R_2$ and $R_3$ are methyl and A denotes the ring systems indicated.

The novel compounds I possess fungicidal, acaricidal and insecticidal properties and are suitable as agrochemical active ingredients for use in agriculture.

The invention additionally relates to a process for the preparation of the novel compounds, and to the fungicidal, acaricidal and insecticidal compositions comprising such compounds as active ingredients, and also to the use of such compounds and compositions for controlling phytopathogenic fungi, acarids and insects and for preventing infestation by fungi, acarids and insects.

Where the compounds of the formula I comprise asymmetric carbon atoms, they occur in optically active form. Solely on the basis of the presence of the aliphatic double bonds and the oximino double bonds, the compounds in any case occur in [E] and/or [Z] forms. Atropic isomerism can occur. The formula I is intended to embrace all of these possible isomeric forms and their mixtures, for example racemic mixtures and any desired [E/Z] mixtures.

Depending on the number of carbon atoms, alkyl and alkoxy groups are straight-chain or branched and are for example methyl, ethyl, n-propyl, isopropyl, n-butyl, sec-butyl, isobutyl, tert-butyl, n-pentyl, neopentyl, sec-pentyl, tert-pentyl, n-hexyl, etc.

Cycloalkyl is cyclopropyl, cyclobutyl, cyclopentyl or cyclohexyl.

Alkenyl is straight-chain or branched alkenyl, for example vinyl, 1-methylvinyl, allyl, 1-butenyl or isopropenyl.

Alkynyl is for example ethynyl, 1-propynyl, 1-butynyl or 1,3-butadiynyl.

Halogen is fluorine, chlorine, bromine or iodine, preferably fluorine, chlorine or bromine.

Haloalkyl can contain identical or different halogen atoms.

Aryl is phenyl or naphthyl, preferably phenyl.

Heteroaryl is groups having 5 to 9 ring members in one or two rings, 1 to 3 of which members are heteroatoms selected from the group consisting of oxygen, sulfur and nitrogen. It is possible for 1 or 2 benzo rings to be fused onto the heterocycle, attachment to the remainder of the molecule being via either the heterocyclic moiety or the benzo moiety.

Examples which could be mentioned are benzimidazolyl, benzisoxazolyl, benzisothiazolyl, benzocoumarinyl, benzofuryl, benzothiadiazolyl, benzothiazolyl, benzothienyl, benzoxazolyl, benzoxdiazolyl, quinazolinyl, quinolyl, quinoxalinyl, carbazolyl, dihydrobenzofuryl, furyl, imidazolyl, indazolyl, indolyl, isoquinolinyl, isothiazolyl, isoxazolyl, methylenedioxyphenyl, ethylenedioxyphenyl, naphthyridinyl, oxazolyl, phenanthridinyl, phthalazinyl, pteridinyl, purinyl, pyrazinyl, pyrazolyl, pyridazinyl, pyrazolo[3,4-b]pyridyl, pyridyl, pyrimidinyl, pyrrolyl, tetrazolyl, oxadiazolyl, thiadiazolyl, thiazolyl, thienyl, triazinyl and triazolyl.

Pyridyl, pyrazinyl, pyrimidinyl, thiazolyl, quinolyl and thienyl are preferred.

Heterocyclyl is a 5- to 7-membered nonaromatic ring having from 1 to 3 heteroatoms selected from the group consisting of N, O and S. Preference is given to aromatic 5- and 6-membered rings containing a nitrogen atom as heteroatom and, if desired, a further heteroatom, preferably nitrogen or sulfur, especially nitrogen.

Thiazolinyl and oxazolinyl are preferred.

A) A compound of the formula I can be prepared by reacting an oxime of the general formula

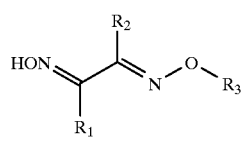

II in which $R_1$, $R_2$ and $R_3$ are as defined for formula I with a benzyl derivative of the general formula

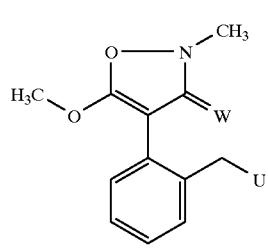

III or, respectively,

-continued

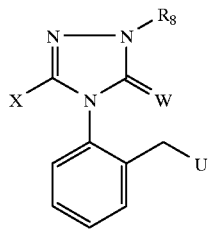

IV in which W is as defined for formula I and U is a leaving group.

This reaction is a nucleophilic substitution which can be carried out under the customary conditions for such reactions. The leaving group U present in the benzyl derivative of the formula III or IV is preferably chlorine, bromine, iodine, mesyloxy or tosyloxy. Reaction takes place advantageously in an inert organic diluent such as a cyclic ether, for example tetrahydrofuran or dioxane, acetone, dimethylformamide or dimethylsulfoxide, in the presence of a base, such as sodium hydride, sodium or potassium carbonate, sodium amide, a tertiary amine, for example a trialkylamine, especially diazabicyclononane or diazabicycloundecane, or silver oxide, at temperatures between −20° C. and +80° C., preferably in the temperature range from 0° C. to 50° C.

Alternatively, the reaction can be carried out under phase transfer catalysis in an organic solvent such as, for example, methylene chloride or toluene, in the presence of an aqueous basic solution, for example sodium hydroxide solution, and of a phase transfer catalyst, for example tetrabutylammonium hydrogen sulfate, at room temperature.

The compounds of the formula I thus prepared can be isolated and purified by methods known per se. Isomer mixtures obtained, for example E/Z isomer mixtures, can be resolved into the pure isomers likewise by methods which are known per se, for example by chromatography or fractional crystallization.

The oximes of the general formula II used as starting materials are either known or can be prepared by known methods (J. Chem. Soc., Perkin Trans. II 537 (1990); Ber. Deutsch. Chem. Ges. 62, 866 (1929); Gazz. Chim. Ital. 37 II, 147 (1907); Liebigs Ann. Chem. 262, 305 (1891)).

Similarly, the benzyl derivatives of the general formulae III and IV used as starting materials are either known or can be prepared by known methods.

B) The compounds of the general formula I in which $R_1$–$R_3$ are as defined and W is sulfur can additionally be prepared by carefully reacting compounds of the general formula I in which W is oxygen with a sulfurization reagent, for example $P_2S_5$, or Lawesson's reagent, for example 2,4-bis(4-methoxyphenyl)-1,3-dithia-2,4-diphosphetane 2,4-disulfide (see in this context Cava+Lawesson, Tetrahedron 41, 5061 (1985)).

C) The compounds of the formula I in which A is the group

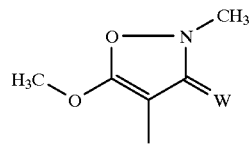

and W is oxygen can additionally be prepared in accordance with scheme 1 below.

The individual reaction steps can be carried out in analogy to those described by Rolf H. Prager and Jason A. Smith in Aust. J. Chem. 48, 217–226 (1995).

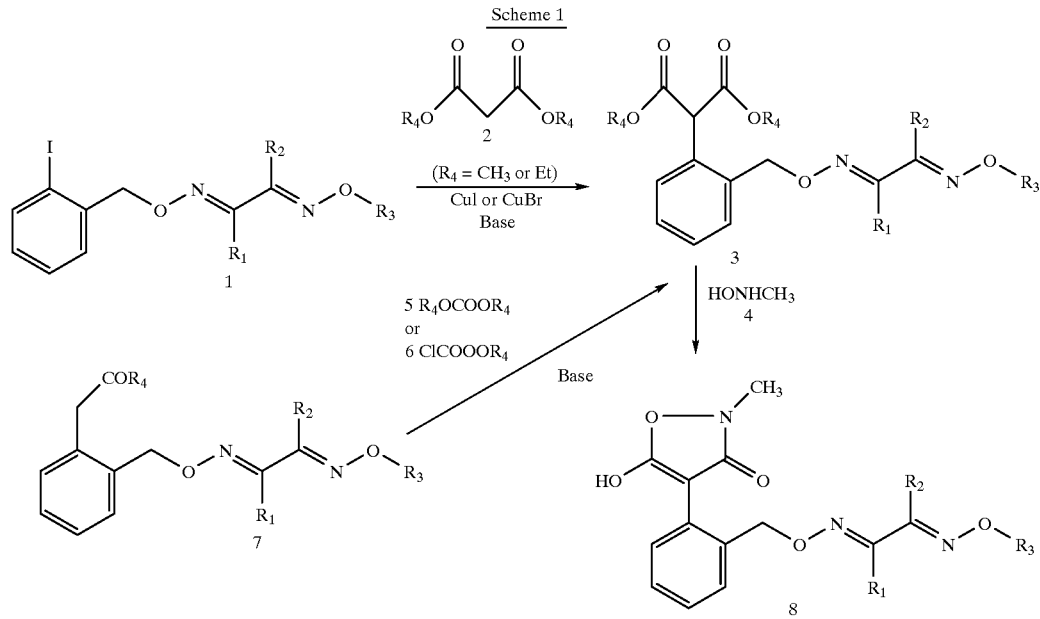
Scheme 1

-continued

9  Dimethyl sulfate or
10 Methyl iodide or        Base
11 (CH$_3$)$_3$OBF$_4$ or
12 Q—CH=N$_2$
    Q = H or (CH$_3$)$_3$Si

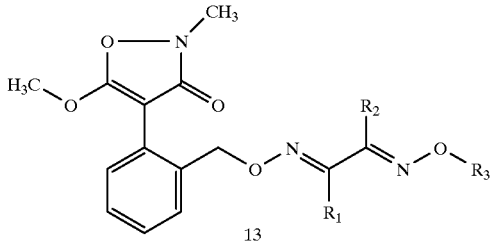

13

As can be seen, the malonic ester derivatives of the formula 3 and the isoxazolone derivatives of the formula 8 are important intermediates and are a further subject of the present invention.

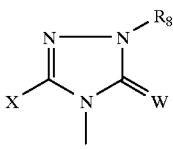

20

D) The compounds of the formula I in which A is the group can additionally be prepared in accordance with scheme 2 below.

The individual reaction steps can be carried out in analogy to those described by Arndt et al. in Rev. Fac. Sci. Istanbul [A] 13, 127ff. [Beilstein E III/IV 26, 674].

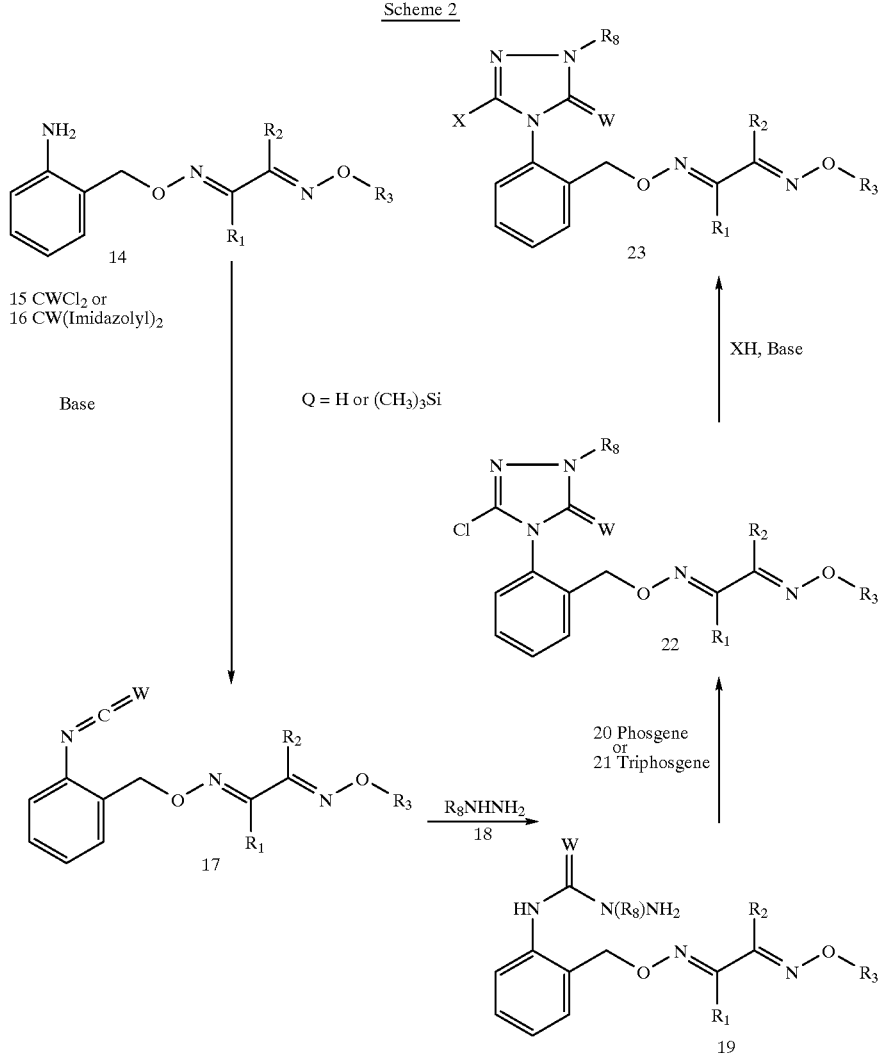

Scheme 2

Compound 1 is obtained by reacting an oxime of the general formula

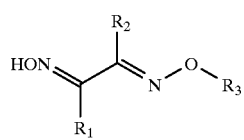

II in which $R_1$–$R_3$ are as defined for formula I with an iodobenzyl derivative of the general formula

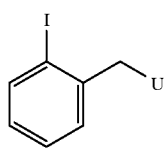

V in which U is a leaving group.

The compound 14 is obtained by subjecting a nitro derivative of the general formula VI to catalytic hydrogenation.

VI

As is evident, the nitrophenyl derivatives of the formula VI, the anilino derivatives of the formula 14, the iso(thio)cyanates of the formula 17 and the (thio)guanidine derivatives of the formula 19 are important intermediates in obtaining (thio)triazolone derivatives of the formulae 22 and 23. The invention relates additionally to these intermediates, in which the substituents $R_1$ to $R_8$, X and W are as defined for formula I.

The compounds of the general formula VI in turn are produced by reacting an oxime of the general formula II with a nitrobenzyl derivative of the general formula

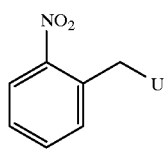

VII in which U is a leaving group.

It has now been found that compounds of the formula I have a microbicidal spectrum which is favourable for practical requirements in the control of phytopathogenic microorganisms, especially fungi. They possess highly advantageous curative, preventive and, in particular, systemic properties and can be employed to protect numerous plants. Using the active ingredients of the formula I, the pests which occur on plants or parts of plants (fruits, flowers, foliage, stems, tubers, roots) of various crops can be contained or destroyed, with protection against phytopathogenic microorganisms remaining for plant parts which develop subsequently as well.

The compounds of the formula I can also be used as dressing agents for treating seeds fruits, tubers, seeds) and plant cuttings, i.e. for treating propagation stock of all kinds, for protection against fungal infection and against phytopathogenic fungi which occur in the soil.

Compounds of the formula I are effective, for example, against the following classes of phytopathogenic fungi: Fungi imperfecti (especially Botrytis, Pyricularia, Helminthosporium, Fusarium, Septoria, Cercospora, Cercosporella and Alternaria); Basidiomycetes (e.g. Rhizoctonia, Hemileia, Puccinia); Ascomycetes (e.g. Venturia and Erysiphe, Podosphaera, Monilinia, Uncinula), but especially against Oomycetes (e.g. Phytophthora, Peronospora, Bremia, Pythium, Plasmopara). Compounds of the formula I also possess an insecticidal and acaricidal action, especially against biting and sucking insects. Target crops for the plant-protecting use disclosed herein are, within the scope of this invention, the following plant types (given by way of example): cereals (wheat, barley, rye, oats, triticale, rice, maize, sorghum and related species); beet crops (sugar beet and fodder beet); pome fruit, stone fruit and soft fruit (apples, pears, plums, peaches, almonds, cherries, strawberries, gooseberries, raspberries and blackberries); legumes (beans, lentils, peas, soya); oil crops (oilseed rape, mustard, poppy, olive, sunflower, coconut, castor, cacao, ground nuts); cucurbits (pumpkin, cucumbers, melons); fibre plants (cotton, flax, hemp, jute); citrus fruits (oranges, lemons, grapefruit, tangerines); vegetables (spinach, lettuce, asparagus, cabbages, carrots, onions, tomatoes, potatoes, bell pepper); the laurel family (avocado, cinnamon, camphor) and plants such as tobacco, nuts, coffee, sugar cane, tea, pepper and other spice plants, vines, hops, egg plants, the banana family, latex plants, and flowers and ornamentals.

Active ingredients of the formula I are customarily used in the form of compositions and can be applied simultaneously or in succession with other active ingredients to the plants or area to be treated. These other active ingredients may be fertilizers, trace element providers or other preparations which influence plant growth. In this context it is also possible to use selective herbicides and also insecticides, fungicides, bactericides, nematicides, molluscicides or mixtures of two or more of these preparations together, if desired, with further carriers, surfactants or other application-promoting additives which are customary in formulation technology, without adversely affecting the activity of the compounds of the formula I.

Suitable carriers and additives can be solid or liquid and correspond to the substances which are expedient in formulation technology, examples being natural or regenerated mineral substances, solvents, dispersants, wetting agents, tackifiers, thickeners, binders or fertilizers.

Suitable solvents are aromatic hydrocarbons, preferably the fractions $C_8$ to $C_{12}$, for example xylene mixtures or substituted naphthalenes, phthalates, such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl ether or ethyl ether, ketones such as cylcohexanone, strongly polar solvents such as N-methyl-2-pyrrolidone, dimethyl sulfoxide or dimethylformamide, and unmodified or epoxidized vegetable oils, such as epoxidized coconut oil or soya oil; or water.

Solid carriers which are generally used, for example for dusts and dispersible powders, are natural ground minerals, such as calcite, talc, kaolin, montmorillonite or attapulgite.

Particularly advantageous application-promoting additives which may result in a greatly reduced rate of application are, moreover, natural (animal or vegetable) or synthetic phospholipids from the series of the cephalins and lecithins, which can be obtained, for example, from soya beans.

Suitable surface-active compounds are, depending on the nature of the active ingredient of the formula I to be formulated, nonionic, cationic and/or anionic surfactants which have good emulsifying, dispersing and wetting properties. The term surfactants is to be understood as including surfactant mixtures.

Suitable anionic surfactants can be so-called water-soluble soaps and also water-soluble synthetic surface-active compounds.

Soaps are the alkali metal salts, alkaline earth metal salts or substituted or unsubstituted ammonium salts of higher fatty acids ($C_{10}$–$C_{22}$), for example the sodium salts or potassium salts of oleic or stearic acid, or of natural fatty acid mixtures which can be obtained, for example, from coconut oil or tallow oil. The fatty acid methyltaurine salts should also be mentioned.

Suitable nonionic surfactants are polyglycol ether derivatives of aliphatic or cycloaliphatic alcohols, saturated or unsaturated fatty acids and alkylphenols which can contain 3 to 30 glycol ether groups and 8 to 20 carbon atoms in the (aliphatic) hydrocarbon radical and 6 to 18 carbon atoms in the alkyl radical of the alkylphenols.

Examples of nonionic surfactants are nonylphenol polyethoxyethanols, castor oil polyglycol ethers, polypropylene-polyethylene oxide adducts, tributylphenoxypolyethoxyethanol, polyethylene glycol and octylphenoxypolyethoxyethanol.

Also suitable are fatty acid esters of polyoxyethylenesorbitan, such as polyoxyethylenesorbitan trioleate.

The cationic surfactants include, in particular, quaternary ammonium salts which as substituent on the nitrogen contain at least one alkyl radical having 8 to 22 carbon atoms, and as further substituents comprise lower, unsubstituted or halogenated alkyl radicals, benzyl radicals or lower hydroxyalkyl radicals.

The anionic, nonionic or cationic surfactants which are familiar in formulation technology are known to the person skilled in the art or can be taken from the relevant technical literature:

"Mc Cutcheon's Detergents and Emulsifiers Annual", Mc Publishing Corp., Glen Rock, New Jersey, 1988.

M. and J. Ash, "Encyclopedia of Surfactants", Vol. I–III, Chemical Publishing Co., New York, 1980–1982.

Dr. Helmut Stache "Tensid-Taschenbuch", Carl Hanser Verlag, Munich/Vienna 1982.

In general, the agrochemical formulations contain from 0.1 to 99%, in particular from 0.1 to 95%, of active ingredient of formula I, from 99.9 to 1%, in particular from 99.9 to 5%, of a solid or liquid additive and from 0 to 25%, in particular from 0.1 to 25%, of a surfactant.

While concentrated compositions tend to be preferred as the commercial product, the end user generally employs dilute compositions.

The compositions can also comprise further additives, such as stabilizers, antifoams, viscosity regulators, binders, tackifiers and fertilizers or other active ingredients for achieving specific effects.

The formulations, i.e. the compositions, preparations or combinations comprising the active ingredient of the formula I together if desired with a solid or liquid additive, are prepared in a known manner, for example by intimately mixing and/or grinding the active ingredient with an extender, for example with a solvent (mixture), a solid carrier material and, if appropriate, surface-active compounds (surfactants).

A preferred process for applying an active ingredient of the formula I or an agrochemical composition comprising at least one of these active ingredients is application to the foliage (foliar application). Frequency and rate of application depend in this case on the level of attack by the pathogen in question. The active ingredients of the formula I, however, can also reach the plant through the root system (systemic action), by the locus of the plant being drenched with a liquid preparation or by the substances being incorporated in solid form into the soil, for example in the form of granules (soil application). In the case of paddy rice, such granules can be metered out into the flooded rice field. The compounds of the formula I can also be applied to seed kernels (coating) by either soaking the kernels in a liquid formulation of the active ingredient or coating them with a solid formulation. In principle, any type of plant propagation material can be protected using compounds of the formula I, examples being the seed, roots, stalks, branches or shoots.

In this context, the compounds of the formula I are used in pure form or, preferably, together with the auxiliaries which are customary in formulation technology. To this end they are expediently processed in a known manner, for example to give emulsion concentrates, spreadable pastes, directly sprayable or dilutable solutions, dilute emulsions, wettable powders, soluble powders, dusts, granules and encapsulated forms (for example in polymeric substances). The methods of application, such as spraying, atomizing, dusting, broadcasting, painting on or pouring, like the nature of the compositions, are selected to suit the intended aims and the prevailing circumstances. Favourable application rates are, in general, from 1 g to 2 kg of active ingredient (a.i.) per hectare, preferably from 25 g to 800 g of a.i./ha and, with particular preference, from 50 g to 400 g of a.i./ha. When used as seed dressing products, dosage rates of from 0.001 g to 1.0 g of active ingredient per kg of seed are advantageously used.

The examples which follow are intended to illustrate the invention in more detail without imposing any restriction thereon.

PREPARATION EXAMPLES

EXAMPLE 1

Preparation of

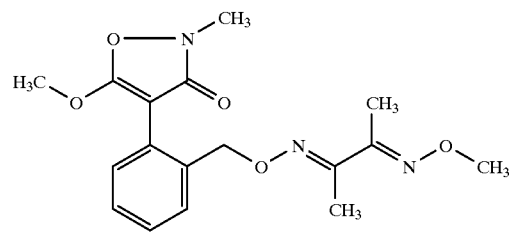

0.22 g of a 60% dispersion of sodium hydride is washed with hexane, and 5 ml of N,N-dimethylformamide are added. 1.5 g of 4-(ortho-bromomethylphenyl)-2,3-dihydro-5-methoxy-2-methyl-3-isoxazolone and 0.65 g of 3-methoximino-2-butanone oxime are added to this suspension and the reaction mixture is stirred for one hour. Then ice-water is added and the mixture is subjected to extraction with ethyl acetate. The organic phase is washed with saturated sodium hydrogen carbonate solution and then with saturated sodium chloride solution. After drying over anhydrons sodium sulfate, the solvent is distilled off in vacuo and the residue is chromatographed on silica gel using ethyl acetate/hexane (1:2), to give Compound No. 1.1; m.p. 100–107° C.

EXAMPLE 2

Preparation of

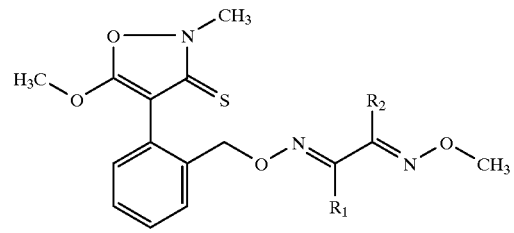

0.7 g of Lawesson's reagent is added to a solution of 1 g of the compound obtained in Example 1 in 10 ml of toluene, and the suspension which forms is then heated at 100° C. for 2 hours. It is then diluted with ethyl acetate and washed with water. The organic phase is dried over sodium sulfate and the solvent is distilled off in vacuo. The residue is chromatographed on silica gel using ethyl acetatelhexane (1:3), to give Compound No. 2.1 as a yellow oil.

EXAMPLE 3

Preparation of

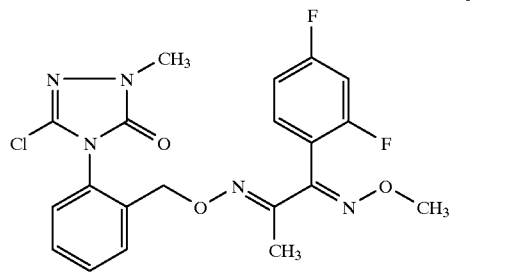

Comp. 6.91 a) 8.95 g of 5-chloro-2-methyl-4-(o-tolyl)-2,4-dihydro[1,2,4]triazol-3-one (prepared according to WO 95/14009) and 7.83 g of N-bromosuccinimide are placed in 50 ml of carbon tetrachloride, and a catalytic amount of dibenzoyl peroxide is added. The suspension is then stirred under reflux with illumination (a 500 W photographic lamp) for 1½ hours. The suspension is concentrated by evaporation and the residue is chromatographed directly on silica gel using hexane/ethyl acetate (6:4). Recrystallization from toluene/heptane (1:1) gives 4-(2-bromomethylphenyl)-5-chloro-2-methyl-2,4-dihydro[1,2,4]triazol-3-one as white crystals of m.p. 131.5–133° C.

$^1$H-NMR (CDCl$_3$) δ 7.52 (m,3H), 7.23 (m,1H), 4.6 (d,1H), 4.33 (d,1H), 3.57 (s,3H).

b) 1.6 g of 1-methoximino-1-(2,4-difluorphenyl)-2-propanone oxime and 2.12 g of 4-(2-bromomethylphenyl)-5-chloro-2-methyl-2,4-dihydro[1,2,4]triazol-3-one are stirred at reflux temperature in the presence of 1.45 g of potassium carbonate in 20 ml of acetonitrile for 2½ hours. The mixture is then concentrated and the residue is chromatographed directly on silica gel using hexane/ethyl acetate (65:35), to give Compound No. 6.91 in a wax-like form.

$^1$H-NMR (CDCl$_3$) δ 7.5–6.7 (m,7H), 5.05 (d,1H), 4.91 (d,1H), 3.93 (s,3H), 3.52 (s,3H), 2.12 (s,3H).

In this way, or by analogy with one of the methods indicated above, it is possible to prepare the following compounds which belong to the narrower range of the present invention.

[$^1$H-NMR: Chemical shifts indicated in δ(ppm) in CDCl$_3$.]

TABLE 1

| Comp. No. | $R_1$ | $R_2$ | $R_3$ | Phys. Data m.p. |
|---|---|---|---|---|
| 1.1 | CH$_3$ | CH$_3$ | CH$_3$ | 100–107° C. |
| 1.2 | CH$_3$ | ▷ | CH$_3$ | |
| 1.3 | CH$_3$ | H | CH$_3$ | |
| 1.4 | CH$_3$ | –C$_6$H$_5$ | CH$_3$ | |
| 1.5 | CH$_3$ | –C$_6$H$_4$–CH$_3$ (4-) | CH$_3$ | |
| 1.6 | CH$_3$ | –C$_6$H$_4$–CH$_3$ (3-) | CH$_3$ | |

TABLE 1-continued

[Structure: methyl isoxazolone with methoxy group, connected to phenyl with CH₂-O-N=C(R₁)-C(R₂)=N-O-R₃]

| Comp. No. | R₁ | R₂ | R₃ | Phys. Data m.p. |
|---|---|---|---|---|
| 1.7 | CH₃ | 2,3-dimethylphenyl | CH₃ | 123–125° C. |
| 1.8 | CH₃ | 4-chlorophenyl | CH₃ | |
| 1.9 | CH₃ | 3-chlorophenyl | CH₃ | |
| 1.10 | CH₃ | 4-fluorophenyl | CH₃ | |
| 1.11 | CH₃ | 3-fluorophenyl | CH₃ | |
| 1.12 | CH₃ | 2,3-difluorophenyl | CH₃ | |
| 1.13 | CH₃ | 4-(trifluoromethyl)phenyl | CH₃ | |
| 1.14 | CH₃ | 3-(trifluoromethyl)phenyl | CH₃ | |

TABLE 1-continued
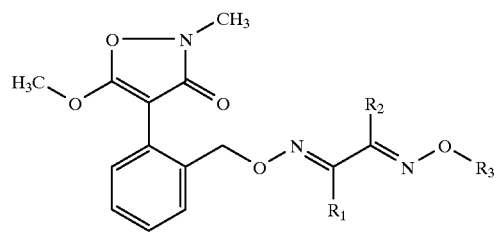
| Comp. No. | R₁ | R₂ | R₃ | Phys. Data m.p. |
|---|---|---|---|---|
| 1.15 | CH₃ | 4-methyl-2-CF₃-1-Cl-phenyl | CH₃ | |
| 1.16 | CH₃ | 4-ethynylphenyl | CH₃ | |
| 1.17 | CH₃ | 4-(cyclopropylmethoxy)phenyl | CH₃ | |
| 1.18 | CH₃ | 4-((2,2-dichloro-1-methylcyclopropyl)methoxy)phenyl | CH₃ | |
| 1.19 | CH₃ | 4-OCH₃-phenyl | CH₃ | |
| 1.20 | CH₃ | 3-OCH(CH₃)₂-phenyl | CH₃ | |
| 1.21 | CH₃ | 3-OCF₃-phenyl | CH₃ | |
| 1.22 | CH₃ | 4-SCH₂CH₂CH₃-phenyl | CH₃ | |

TABLE 1-continued
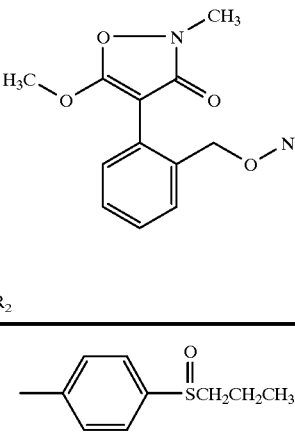
| Comp. No. | R₁ | R₂ | R₃ | Phys. Data m.p. |
|---|---|---|---|---|
| 1.23 | CH₃ | 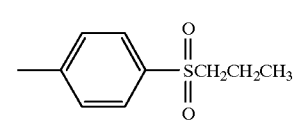 | CH₃ | |
| 1.24 | CH₃ | 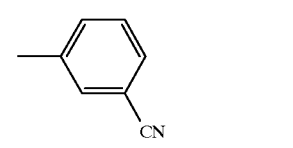 | CH₃ | |
| 1.25 | CH₃ | 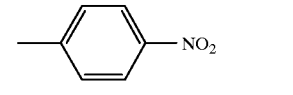 | CH₃ | |
| 1.26 | CH₃ | 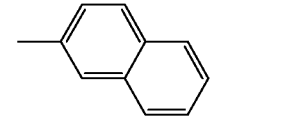 | CH₃ | |
| 1.27 | CH₃ |  | CH₃ | |
| 1.28 | CH₃ | 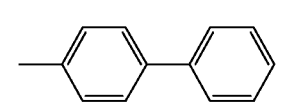 | CH₃ | |
| 1.29 | CH₃ | 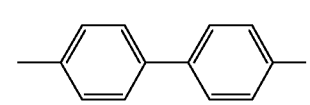 | CH₃ | |
| 1.30 | CH₃ |  | CH₃ | |

TABLE 1-continued

[Structure: 5-methoxy-2-methyl-4-[2-(((R1)C=N-O-CH2)phenyl)]-isoxazol-3(2H)-one with =N-O-R3 and R2 substituent]

| Comp. No. | R1 | R2 | R3 | Phys. Data m.p. |
|---|---|---|---|---|
| 1.31 | CH3 | 4-(phenoxy)phenyl | CH3 | |
| 1.32 | CH3 | 4-((3-chlorophenyl)thio)phenyl | CH3 | |
| 1.33 | CH3 | 4-(3-methylisoxazol-5-yl)phenyl | CH3 | |
| 1.34 | CH3 | CN | CH3 | |
| 1.35 | CH3 | COOCH3 | CH3 | |
| 1.36 | CH3 | SCH3 | CH3 | |
| 1.37 | CH3 | S(O)CH3 | CH3 | |
| 1.38 | CH3 | S(O)2CH3 | CH3 | |
| 1.39 | CH3 | O(CH2)4CH3 | CH3 | |
| 1.40 | CH3 | OC6H5 | CH3 | |
| 1.41 | CH3 | O-(4-chlorophenyl) | CH3 | |
| 1.42 | CH3 | O-(3-chlorophenyl) | CH3 | |
| 1.43 | CH3 | O-(4-trifluoromethylphenyl) | CH3 | |

TABLE 1-continued
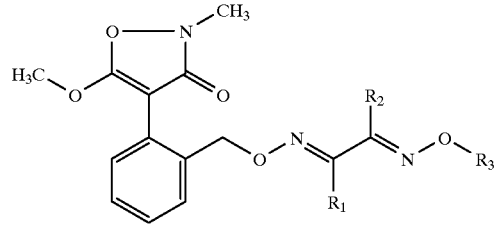
| Comp. No. | R₁ | R₂ | R₃ | Phys. Data m.p. |
|---|---|---|---|---|
| 1.44 | CH₃ | 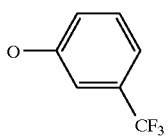 | CH₃ | |
| 1.45 | CH₃ | 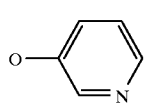 | CH₃ | |
| 1.46 | CH₃ | 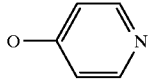 | CH₃ | |
| 1.47 | CH₃ | 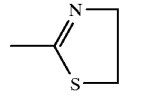 | CH₃ | |
| 1.48 | CH₃ | 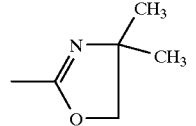 | CH₃ | |
| 1.49 | CH₃ | 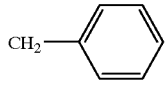 | CH₃ | |
| 1.50 | CH₃ | 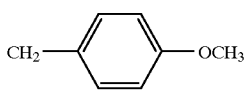 | CH₃ | |
| 1.51 | CH₃ | 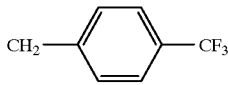 | CH₃ | |
| 1.52 | CH₃ |  | CH₃ | |

TABLE 1-continued
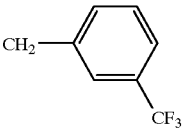
| Comp. No. | $R_1$ | $R_2$ | $R_3$ | Phys. Data m.p. |
|---|---|---|---|---|
| 1.53 | $CH_3$ |  | $CH_3$ | |
| 1.54 | $CH_3$ | 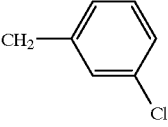 | $CH_3$ | |
| 1.55 | $CH_3$ | 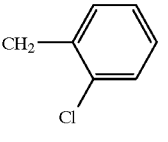 | $CH_3$ | |
| 1.56 | $CH_3$ | 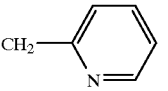 | $CH_3$ | |
| 1.57 | $CH_3$ | 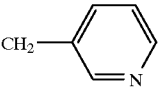 | $CH_3$ | |
| 1.58 | $CH_3$ | 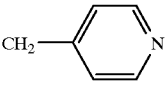 | $CH_3$ | |
| 1.59 | $CH_3$ |  | $CH_3$ | |
| 1.60 | H | $CH_3$ | $CH_3$ | |
| 1.61 | △ | $CH_3$ | $CH_3$ | |
| 1.62 | $CH_3CH_2$ | $CH_3$ | $CH_3$ | |
| 1.63 | $CH_3$ | $CH_3$ | $CH_2CH_3$ | |
| 1.64 | $CH_3$ | $CH_3$ | $CH_2CH_2CH_3$ | |
| 1.65 | $CH_3$ | $CH_3$ | $(CH_2)_3CH_3$ | |
| 1.66 | $CH_3$ | $CH_3$ | $(CH_2)_4CH_3$ | |
| 1.67 | $CH_3$ | $CH_3$ | $(CH_2)_5CH_3$ | |

TABLE 1-continued

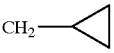

| Comp. No. | $R_1$ | $R_2$ | $R_3$ | Phys. Data m.p. |
|---|---|---|---|---|
| 1.68 | $CH_3$ | $CH_3$ | $CH_2C(CH_3)_3$ | |
| 1.69 | $CH_3$ | $CH_3$ | $CH_2F$ | |
| 1.70 | $CH_3$ | $CH_3$ | $CH_2CF_3$ | |
| 1.71 | $CH_3$ | $CH_3$ | $CH_2CH_2F$ | |
| 1.72 | $CH_3$ | $CH_3$ | $CH_2CH_2CH_2CF_3$ | |
| 1.73 | $CH_3$ | $CH_3$ | $CH_2OCH_3$ | |
| 1.74 | $CH_3$ | $CH_3$ | $CH_2C(Cl)=CH_2$ | |
| 1.75 | $CH_3$ | $CH_3$ | $CH_2$-cyclopropyl | |
| 1.76 | $CH_3$ | $CH_3$ | $CH_2C\equiv CH$ | |
| 1.77 | H | $CH_3$ | $CH_3$ | |
| 1.78 | H | H | $CH_2$-cyclopropyl | |
| 1.79 | H | H | $CH_3$ | |
| 1.80 | $CH_3$ | $CH_3$ | H | |
| 1.81 | $C_2H_5$ | $CH_3$ | H | |
| 1.82 | $CH_3$ | $-C_6H_5$ | H | |
| 1.83 | $CH_3$ | $-CH_2-O-CH_3$ | H | |
| 1.84 | $CH_3$ | $-CH_2-O-CH_3$ | $CH_3$ | |
| 1.85 | $CH_3$ | $-C_6H_4-C_6H_5(p)$ | H | |
| 1.86 | $CH_3$ | $-C_6H_5(4-Cl)$ | H | |
| 1.87 | $CH_3$ | $4-C_6H_4-OnC_3H_7$ | $CH_3$ | |
| 1.88 | $CH_3$ | $4-C_6H_4-OCH_2C_6H_4CF_3(3')$ | $CH_3$ | Oil |
| 1.89 | $CH_3$ | $4-C_6H_4-OisoC_3H_7$ | $CH_3$ | |
| 1.90 | $CH_3$ | $4-C_6H_4-OC_2H_5$ | $CH_3$ | |
| 1.91 | $CH_3$ | $-C_6H_3F_2(2,4)$ | $CH_3$ | |
| 1.92 | $CH_3$ | $4-C_6H_4-OnC_4H_9$ | $CH_3$ | |
| 1.93 | $CH_3$ | $-C_6H_3(CH_3)_2(2,4)$ | $CH_3$ | |
| 1.94 | $CH_3$ | $-C_6H_3(CH_3)_2(2,3)$ | $CH_3$ | |
| 1.95 | $CH_3$ | $-C_6H_3(CH_3)_2(2,5)$ | $CH_3$ | |
| 1.96 | $CH_3$ | $-C_6H_3CH_3(2),F(4)$ | $CH_3$ | |
| 1.97 | $CH_3$ | $-C_6H_3CH_3(2),F(5)$ | $CH_3$ | |
| 1.98 | $CH_3$ | $4-C_6H_4-O-C_6H_4CF_3(3)$ | $CH_3$ | |
| 1.99 | $CH_3$ | $4-C_6H_4-O-C_6H_4Cl(4)$ | $CH_3$ | |
| 1.100 | $CH_3$ | $4-C_6H_4-O-Allyl$ | $CH_3$ | |
| 1.101 | $CH_3$ | $4-C_6H_4-OCF_3$ | $CH_3$ | |
| 1.102 | $CH_3$ | $4-C_6H_4-OCH_2Si(CH_3)_3$ | $CH_3$ | |
| 1.103 | $CH_3$ | $4-C_6H_4-OCH_3$ | $CH_3$ | |
| 1.104 | $CH_3$ | $4-C_6H_4-Osec.C_4H_9$ | $CH_3$ | |
| 1.105 | $CH_3$ | $4-C_6H_4-OisoC_4H_9$ | $CH_3$ | |
| 1.106 | $CH_3$ | $4-C_6H_4-OCH=CCl_2$ | $CH_3$ | |
| 1.107 | $CH_3$ | $4-C_6H_4-ON=C(CH_3)_2$ | $CH_3$ | |
| 1.108 | $CH_3$ | $4-C_6H_4-O-Cyclopentyl$ | $CH_3$ | |
| 1.109 | $CH_3$ | $-C_6H_3F(2)-OnC_3H_7(4)$ | $CH_3$ | |
| 1.110 | $CH_3$ | $-C_6H_3F(2)-OC_2H_5(4)$ | $CH_3$ | |
| 1.111 | $CH_3$ | $-C_6H_3F(2)-OisoC_3H_7(4)$ | $CH_3$ | |
| 1.112 | $CH_3$ | $-C_6H_3F(2)-OCH_3(4)$ | $CH_3$ | |

TABLE 1-continued

| Comp. No. | $R_1$ | $R_2$ | $R_3$ | Phys. Data m.p. |
|---|---|---|---|---|
| 1.113 | $CH_3$ | [3-fluoro-4-methylphenoxymethyl-2,2-dichlorocyclopropyl] | $CH_3$ | |
| 1.114 | $CH_3$ | —$C_6H_3OCH_3(2)F(4)$ | $CH_3$ | |
| 1.115 | $CH_3$ | —$C_6H_3OCH_3(2)CH_3(4)$ | $CH_3$ | |
| 1.116 | $CH_3$ | —$C_6H_3CH_3(2)$-$OCH_3(4)$ | $CH_3$ | |
| 1.117 | $CH_3$ | —$C_6H_3CH_3(2)$-$OC_2H_5(4)$ | $CH_3$ | |
| 1.118 | $CH_3$ | —$C_6H_3CH_3(2)$-$OnC_3H_7(4)$ | $CH_3$ | |
| 1.119 | $CH_3$ | —$C_6H_3CH_3(2)$-$OisoC_3H_7(4)$ | $CH_3$ | |
| 1.120 | $CH_3$ | —$C_6H_4$—$OnC_3H_7(4)$ | $CH_2CH_3$ | |
| 1.121 | $CH_3$ | —$C_6H_4$—$OC_2H_5(4)$ | $CH_2CH_3$ | |
| 1.122 | $CH_3$ | —$C_6H_4$—$OnC_3H_7(4)$ | $CH_2F$ | |
| 1.123 | $CH_3$ | —$C_6H_4$—$OnC_3H_7(4)$ | $CH_2$—$C{\equiv}CH$ | |
| 1.124 | $CH_3$ | —$C_6H_4$—$OnC_3H_7(4)$ | $(CH_2)_2CH_3$ | |
| 1.125 | $CH_3$ | —$C_6H_4$—$OnC_3H_7(4)$ | $CH(CH_3)_2$ | |
| 1.126 | $CH_3$ | —$C_6H_4$—$OnC_3H_7(4)$ | $CH_2$—$CH{=}CH_2$ | |
| 1.127 | $CH_3$ | 2-Tolyl | $CH_2CH_3$ | |
| 1.128 | $CH_3$ | —$C_6H_3F(2)CH_3(4)$ | $CH_3$ | |
| 1.129 | $CH_3$ | —$C_6H_3F(2)CH_3(5)$ | $CH_3$ | |
| 1.130 | $CH_3$ | —$C_6H_3F_2(2,5)$ | $CH_3$ | |
| 1.131 | $CH_3$ | —$C_6H_4$—$OCH_2CF_3(4)$ | $CH_3$ | |
| 1.132 | $CH_3$ | —$C_6H_4C_2H_5(4)$ | $CH_3$ | |
| 1.133 | $CH_3$ | —$COOCH_2CH{=}CH_2$ | $CH_3$ | |
| 1.134 | $CH_3$ | —$C_6H_4$—$OCHF_2(4)$ | $CH_3$ | |
| 1.135 | $CH_3$ | 4-$C_6H_4$—O—$C_6H_4F(4')$ | $CH_3$ | |
| 1.136 | $CH_3$ | —$COOCH(CH_3)_2$ | $CH_3$ | |
| 1.137 | $CH_3$ | —$C_6H_4Br(4)$ | $CH_3$ | |
| 1.138 | $CH_3$ | 2-Pyridyl | $CH_3$ | |
| 1.139 | $CH_3$ | 3-Pyridyl | $CH_3$ | |
| 1.140 | $CH_3$ | 4-Pyridyl | $CH_3$ | |
| 1.141 | $CH_3$ | 2-Pyrazinyl | $CH_3$ | |
| 1.142 | $CH_3$ | 5,6-Dichloropyridinyl(3) | $CH_3$ | |
| 1.143 | $CH_3$ | $CH_3$ | $CF_2CHF_2$ | |
| 1.144 | $CH_3$ | 2-Fluoro-4-(4'-fluorobenzyloxy)-phenyl | $CH_3$ | |
| 1.145 | $CH_3$ | 4-$C_6H_4$—O—$C_6H_4Br(3')$ | $CH_3$ | |
| 1.146 | $CH_3$ | —$C_6H_5$ | $CH_2C{\equiv}CH$ | |

TABLE 2
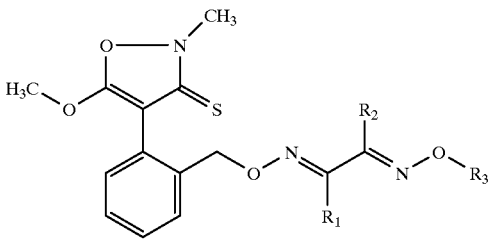
| Comp. No. | R₁ | R₂ | R₃ | Phys. Data |
|---|---|---|---|---|
| 2.1 | CH₃ | CH₃ | CH₃ | Oil |
| 2.2 | CH₃ | cyclopropyl | CH₃ | |
| 2.3 | CH₃ | H | CH₃ | |
| 2.4 | CH₃ | phenyl | CH₃ | |
| 2.5 | CH₃ | 4-CH₃-phenyl | CH₃ | |
| 2.6 | CH₃ | 3-CH₃-phenyl | CH₃ | |
| 2.7 | CH₃ | 2-CH₃-phenyl | CH₃ | |
| 2.8 | CH₃ | 4-Cl-phenyl | CH₃ | |
| 2.9 | CH₃ | 3-Cl-phenyl | CH₃ | |
| 2.10 | CH₃ | 4-F-phenyl | CH₃ | |

TABLE 2-continued
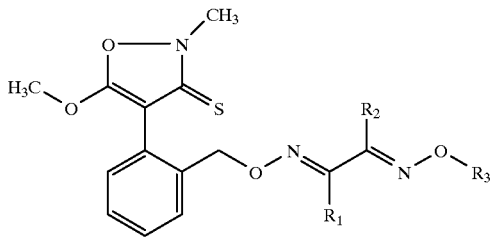
| Comp. No. | R₁ | R₂ | R₃ | Phys. Data |
|---|---|---|---|---|
| 2.11 | CH₃ | 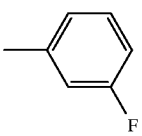 | CH₃ | |
| 2.12 | CH₃ | 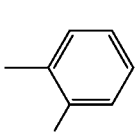 | CH₃ | |
| 2.13 | CH₃ | 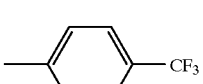 | CH₃ | |
| 2.14 | CH₃ | 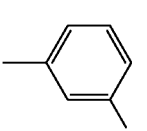 | CH₃ | |
| 2.15 | CH₃ | 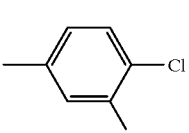 | CH₃ | |
| 2.16 | CH₃ | 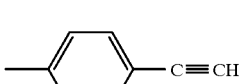 | CH₃ | |
| 2.17 | CH₃ | 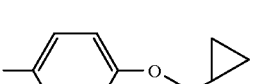 | CH₃ | |
| 2.18 | CH₃ | 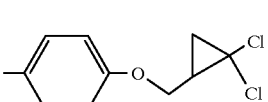 | CH₃ | |

TABLE 2-continued
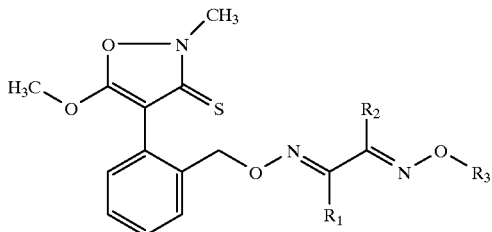
| Comp. No. | $R_1$ | $R_2$ | $R_3$ | Phys. Data |
|---|---|---|---|---|
| 2.19 | $CH_3$ | 4-$OCH_3$-phenyl | $CH_3$ | |
| 2.20 | $CH_3$ | 3-$OCH(CH_3)_2$-phenyl | $CH_3$ | |
| 2.21 | $CH_3$ | 3-$OCF_3$-phenyl | $CH_3$ | |
| 2.22 | $CH_3$ | 4-$SCH_2CH_2CH_3$-phenyl | $CH_3$ | |
| 2.23 | $CH_3$ | 4-$S(O)CH_2CH_2CH_3$-phenyl | $CH_3$ | |
| 2.24 | $CH_3$ | 4-$S(O)_2CH_2CH_2CH_3$-phenyl | $CH_3$ | |
| 2.25 | $CH_3$ | 3-$CN$-phenyl | $CH_3$ | |
| 2.26 | $CH_3$ | 4-$NO_2$-phenyl | $CH_3$ | |

TABLE 2-continued
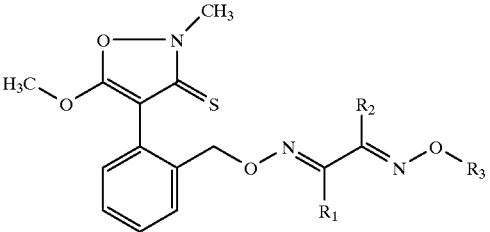
| Comp. No. | $R_1$ | $R_2$ | $R_3$ | Phys. Data |
|---|---|---|---|---|
| 2.27 | $CH_3$ | 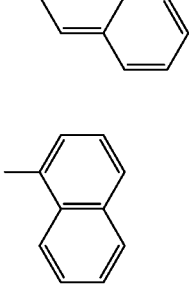 | $CH_3$ | |
| 2.28 | $CH_3$ | 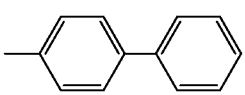 | $CH_3$ | |
| 2.29 | $CH_3$ | 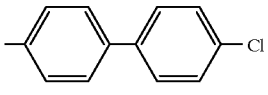 | $CH_3$ | |
| 2.30 | $CH_3$ | 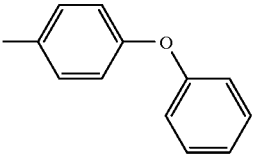 | $CH_3$ | |
| 2.31 | $CH_3$ | 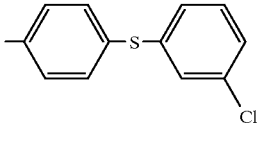 | $CH_3$ | |
| 2.32 | $CH_3$ | 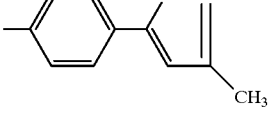 | $CH_3$ | |
| 2.33 | $CH_3$ |  | $CH_3$ | |
| 2.34 | $CH_3$ | CN | $CH_3$ | |
| 2.35 | $CH_3$ | $COOCH_3$ | $CH_3$ | |
| 2.36 | $CH_3$ | $SCH_3$ | $CH_3$ | |
| 2.37 | $CH_3$ | $S(O)CH_3$ | $CH_3$ | |
| 2.38 | $CH_3$ | $S(O)_2CH_3$ | $CH_3$ | |
| 2.39 | $CH_3$ | $O(CH_2)_4CH_3$ | $CH_3$ | |

TABLE 2-continued
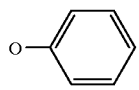
| Comp. No. | R₁ | R₂ | R₃ | Phys. Data |
|---|---|---|---|---|
| 2.40 | CH₃ | 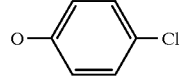 | CH₃ | |
| 2.41 | CH₃ | 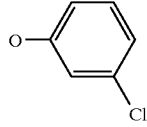 | CH₃ | |
| 2.42 | CH₃ | 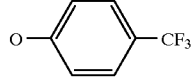 | CH₃ | |
| 2.43 | CH₃ | 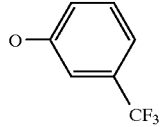 | CH₃ | |
| 2.44 | CH₃ | 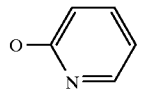 | CH₃ | |
| 2.45 | CH₃ | 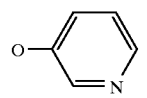 | CH₃ | |
| 2.46 | CH₃ | 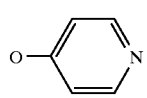 | CH₃ | |
| 2.47 | CH₃ | 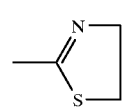 | CH₃ | |
| 2.48 | CH₃ |  | CH₃ | |

TABLE 2-continued
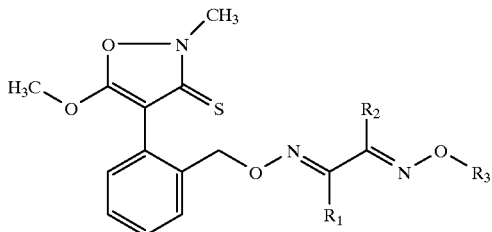
| Comp. No. | R₁ | R₂ | R₃ | Phys. Data |
|---|---|---|---|---|
| 2.49 | CH₃ | 2,4,4-trimethyl-4,5-dihydrooxazol-2-yl group | CH₃ | |
| 2.50 | CH₃ | CH₂-phenyl | CH₃ | |
| 2.51 | CH₃ | CH₂-(4-OCH₃-phenyl) | CH₃ | |
| 2.52 | CH₃ | CH₂-(4-CF₃-phenyl) | CH₃ | |
| 2.53 | CH₃ | CH₂-(3-CF₃-phenyl) | CH₃ | |
| 2.54 | CH₃ | CH₂-(4-Cl-phenyl) | CH₃ | |
| 2.55 | CH₃ | CH₂-(3-Cl-phenyl) | CH₃ | |
| 2.56 | CH₃ | CH₂-(2-Cl-phenyl) | CH₃ | |

TABLE 2-continued

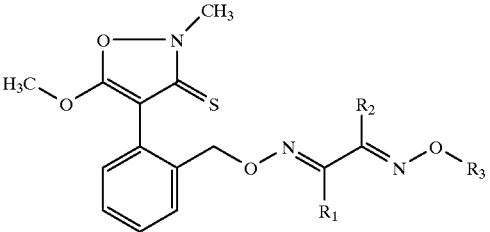

| Comp. No. | $R_1$ | $R_2$ | $R_3$ | Phys. Data |
|---|---|---|---|---|
| 2.57 | $CH_3$ | 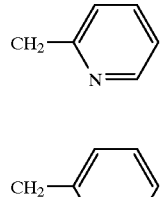 | $CH_3$ | |
| 2.58 | $CH_3$ | 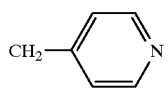 | $CH_3$ | |
| 2.59 | $CH_3$ |  | $CH_3$ | |
| 2.60 | H | $CH_3$ | $CH_3$ | |
| 2.61 | 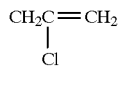 | $CH_3$ | $CH_3$ | |
| 2.62 | $CH_3CH_2$ | $CH_3$ | $CH_3$ | |
| 2.63 | $CH_3$ | $CH_3$ | $CH_2CH_3$ | |
| 2.64 | $CH_3$ | $CH_3$ | $CH_2CH_2CH_3$ | |
| 2.65 | $CH_3$ | $CH_3$ | $(CH_2)_3CH_3$ | |
| 2.66 | $CH_3$ | $CH_3$ | $(CH_2)_4CH_3$ | |
| 2.67 | $CH_3$ | $CH_3$ | $(CH_2)_5CH_3$ | |
| 2.68 | $CH_3$ | $CH_3$ | $CH_2C(CH_3)_3$ | |
| 2.69 | $CH_3$ | $CH_3$ | $CH_2F$ | |
| 2.70 | $CH_3$ | $CH_3$ | $CH_2CF_3$ | |
| 2.71 | $CH_3$ | $CH_3$ | $CH_2CH_2F$ | |
| 2.72 | $CH_3$ | $CH_3$ | $CH_2CH_2CH_2CF_3$ | |
| 2.73 | $CH_3$ | $CH_3$ | $CH_2OCH_3$ | |
| 2.74 | $CH_3$ | $CH_3$ | 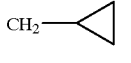 | |
| 2.75 | $CH_3$ | $CH_3$ | 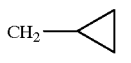 | |
| 2.76 | $CH_3$ | $CH_3$ | $CH_2C{\equiv}CH$ | |
| 2.77 | H | $CH_3$ | $CH_3$ | |
| 2.78 | H | H |  | |
| 2.79 | H | H | $CH_3$ | |
| 2.80 | $CH_3$ | $CH_3$ | H | |
| 2.81 | $C_2H_5$ | $CH_3$ | H | |
| 2.82 | $CH_3$ | —$C_6H_5$ | H | |
| 2.83 | $CH_3$ | —$CH_2$—O—$CH_3$ | H | |
| 2.84 | $CH_3$ | —$CH_2$—O—$CH_3$ | $CH_3$ | |

TABLE 2-continued
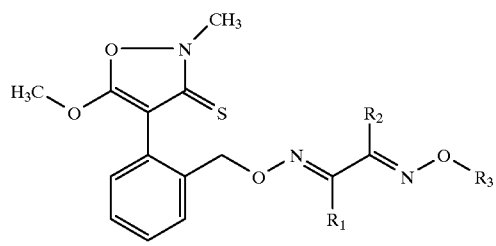
| Comp. No. | R$_1$ | R$_2$ | R$_3$ | Phys. Data |
|---|---|---|---|---|
| 2.85 | CH$_3$ | —C$_6$H$_4$—C$_6$H$_5$(p) | H | |
| 2.86 | CH$_3$ | —C$_6$H$_5$(4-Cl) | H | |
TABLE 3
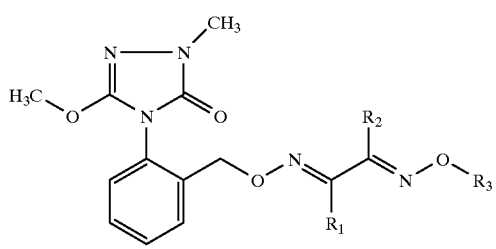
| Comp. No. | R$_1$ | R$_2$ | R$_3$ | Phys. Data m.p. |
|---|---|---|---|---|
| 3.1 | CH$_3$ | CH$_3$ | CH$_3$ | 127–129° C. |
| 3.2 | CH$_3$ | ▷ | CH$_3$ | |
| 3.3 | CH$_3$ | H | CH$_3$ | |
| 3.4 | CH$_3$ | —C$_6$H$_5$ | CH$_3$ | |
| 3.5 | CH$_3$ | —C$_6$H$_4$—CH$_3$ (p) | CH$_3$ | Oil |
| 3.6 | CH$_3$ | —C$_6$H$_4$—CH$_3$ (m) | CH$_3$ | |
| 3.7 | CH$_3$ | —C$_6$H$_4$—CH$_3$ (o) | CH$_3$ | 122–125° C. |

TABLE 3-continued
| Comp. No. | R₁ | R₂ | R₃ | Phys. Data m.p. |
|---|---|---|---|---|
| 3.8 | CH₃ | 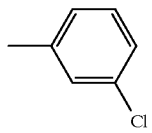 4-Cl-C₆H₄ | CH₃ | |
| 3.9 | CH₃ |  3-Cl-C₆H₄ | CH₃ | |
| 3.10 | CH₃ | 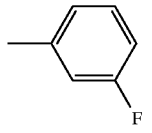 4-F-C₆H₄ | CH₃ | |
| 3.11 | CH₃ | 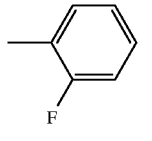 3-F-C₆H₄ | CH₃ | |
| 3.12 | CH₃ | 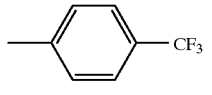 2-F-C₆H₄ | CH₃ | |
| 3.13 | CH₃ | 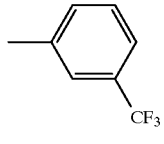 4-CF₃-C₆H₄ | CH₃ | 113–115° C. |
| 3.14 | CH₃ | 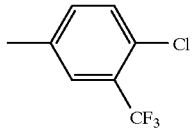 3-CF₃-C₆H₄ | CH₃ | |
| 3.15 | CH₃ | 4-Cl-3-CF₃-C₆H₃ | CH₃ | |

TABLE 3-continued
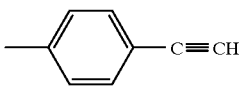
| Comp. No. | R₁ | R₂ | R₃ | Phys. Data m.p. |
|---|---|---|---|---|
| 3.16 | CH₃ | 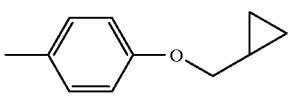 | CH₃ | Oil |
| 3.17 | CH₃ | 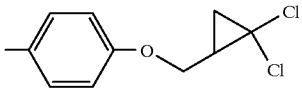 | CH₃ | |
| 3.18 | CH₃ | 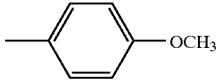 | CH₃ | |
| 3.19 | CH₃ | 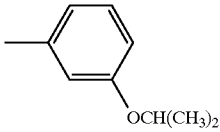 | CH₃ | 115–126° C. |
| 3.20 | CH₃ | 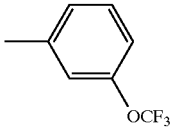 | CH₃ | Oil |
| 3.21 | CH₃ | 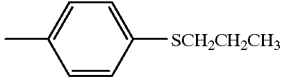 | CH₃ | |
| 3.22 | CH₃ | 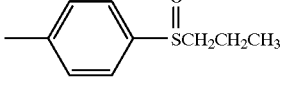 | CH₃ | |
| 3.23 | CH₃ | 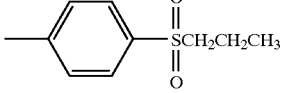 | CH₃ | |
| 3.24 | CH₃ |  | CH₃ | |

TABLE 3-continued
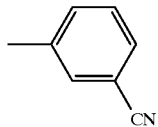
| Comp. No. | R₁ | R₂ | R₃ | Phys. Data m.p. |
|---|---|---|---|---|
| 3.25 | CH₃ | 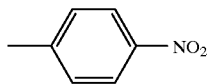 | CH₃ | |
| 3.26 | CH₃ | 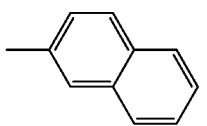 | CH₃ | |
| 3.27 | CH₃ | 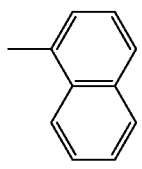 | CH₃ | |
| 3.28 | CH₃ | 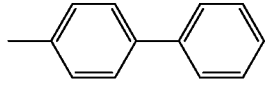 | CH₃ | |
| 3.29 | CH₃ | 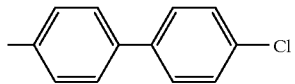 | CH₃ | Oil |
| 3.30 | CH₃ | 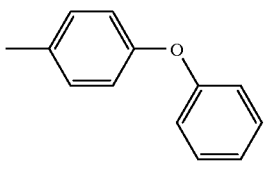 | CH₃ | |
| 3.31 | CH₃ |  | CH₃ | |

TABLE 3-continued

[Structure: 1,2,4-triazol-3(2H)-one with N-CH3, 5-OCH3, and N4-linked to 2-(aminooxymethyl)phenyl group connected via O—N=C(R1)—C(R2)=N—O—R3]

| Comp. No. | R₁ | R₂ | R₃ | Phys. Data m.p. |
|---|---|---|---|---|
| 3.32 | CH₃ | 4-CH₃-C₆H₄-S-C₆H₄-3-Cl | CH₃ | |
| 3.33 | CH₃ | 5-(4-CH₃-C₆H₄)-3-CH₃-isoxazol-yl | CH₃ | |
| 3.34 | CH₃ | CN | | |
| 3.35 | CH₃ | COOCH₃ | CH₃ | |
| 3.36 | CH₃ | SCH₃ | CH₃ | |
| 3.37 | CH₃ | S(O)CH₃ | CH₃ | |
| 3.38 | CH₃ | S(O)₂CH₃ | CH₃ | |
| 3.39 | CH₃ | O(CH₂)₄CH₃ | CH₃ | |
| 3.40 | CH₃ | O-C₆H₅ | CH₃ | |
| 3.41 | CH₃ | O-C₆H₄-4-Cl | CH₃ | |
| 3.42 | CH₃ | O-C₆H₄-3-Cl | CH₃ | |
| 3.43 | CH₃ | O-C₆H₄-4-CF₃ | CH₃ | |
| 3.44 | CH₃ | O-C₆H₄-3-CF₃ | CH₃ | |

TABLE 3-continued
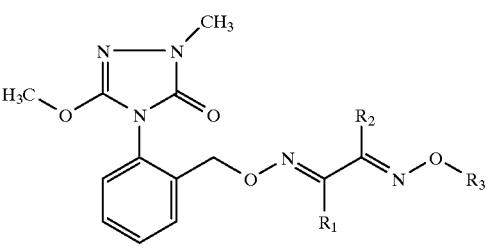
| Comp. No. | R₁ | R₂ | R₃ | Phys. Data m.p. |
|---|---|---|---|---|
| 3.45 | CH₃ | 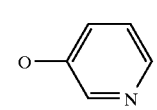 | CH₃ | |
| 3.46 | CH₃ | 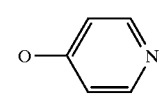 | CH₃ | |
| 3.47 | CH₃ | 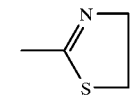 | CH₃ | |
| 3.48 | CH₃ | 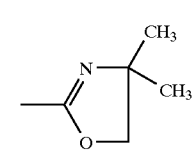 | CH₃ | |
| 3.49 | CH₃ | 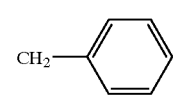 | CH₃ | |
| 3.50 | CH₃ | 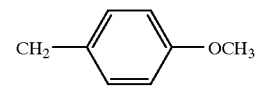 | CH₃ | |
| 3.51 | CH₃ | 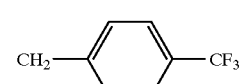 | CH₃ | |
| 3.52 | CH₃ | 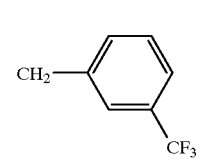 | CH₃ | |
| 3.53 | CH₃ |  | CH₃ | |

TABLE 3-continued

[Structure: methoxy-methyl-triazolone attached to phenyl-CH2-O-N=C(R1)-C(R2)=N-O-R3]

| Comp. No. | R₁ | R₂ | R₃ | Phys. Data m.p. |
|---|---|---|---|---|
| 3.54 | $CH_3$ | $CH_2$-(4-Cl-C₆H₄) | $CH_3$ | |
| 3.55 | $CH_3$ | $CH_2$-(3-Cl-C₆H₄) | $CH_3$ | |
| 3.56 | $CH_3$ | $CH_2$-(2-Cl-C₆H₄) | $CH_3$ | |
| 3.57 | $CH_3$ | $CH_2$-(2-pyridyl) | $CH_3$ | |
| 3.58 | $CH_3$ | $CH_2$-(3-pyridyl) | $CH_3$ | |
| 3.59 | $CH_3$ | $CH_2$-(4-pyridyl) | $CH_3$ | |
| 3.60 | H | $CH_3$ | $CH_3$ | |
| 3.61 | cyclopropyl | $CH_3$ | $CH_3$ | |
| 3.62 | $CH_3CH_2$ | $CH_3$ | $CH_3$ | |
| 3.63 | $CH_3$ | $CH_3$ | $CH_2CH_3$ | |
| 3.64 | $CH_3$ | $CH_3$ | $CH_2CH_2CH_3$ | |
| 3.65 | $CH_3$ | $CH_3$ | $(CH_2)_3CH_3$ | |
| 3.66 | $CH_3$ | $CH_3$ | $(CH_2)_4CH_3$ | |
| 3.67 | $CH_3$ | $CH_3$ | $(CH_2)_5CH_3$ | |
| 3.68 | $CH_3$ | $CH_3$ | $CH_2C(CH_3)_3$ | |
| 3.69 | $CH_3$ | $CH_3$ | $CH_2F$ | |
| 3.70 | $CH_3$ | $CH_3$ | $CH_2CF_3$ | |
| 3.71 | $CH_3$ | $CH_3$ | $CH_2CH_2F$ | |
| 3.72 | $CH_3$ | $CH_3$ | $CH_2CH_2CH_2CF_3$ | |
| 3.73 | $CH_3$ | $CH_3$ | $CH_2OCH_3$ | |

TABLE 3-continued

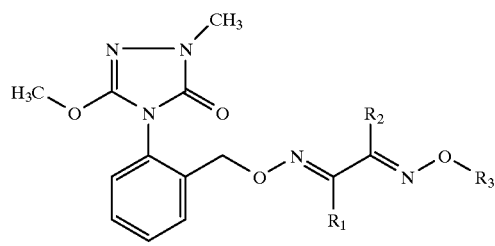

| Comp. No. | R₁ | R₂ | R₃ | Phys. Data m.p. |
|---|---|---|---|---|
| 3.74 | CH₃ | CH₃ | CH₂C=CH₂ with Cl | |
| 3.75 | CH₃ | CH₃ | CH₂-cyclopropyl | |
| 3.76 | CH₃ | CH₃ | CH₂C≡CH | |
| 3.77 | H | CH₃ | CH₃ | |
| 3.78 | H | H | CH₂-cyclopropyl | |
| 3.79 | H | H | CH₃ | |
| 3.80 | CH₃ | CH₃ | H | |
| 3.81 | C₂H₅ | CH₃ | H | |
| 3.82 | CH₃ | —C₆H₅ | H | |
| 3.83 | CH₃ | —CH₂—O—CH₃ | H | |
| 3.84 | CH₃ | —CH₂—O—CH₃ | CH₃ | |
| 3.85 | CH₃ | —C₆H₄—C₆H₅(p) | H | |
| 3.86 | CH₃ | —C₆H₅(4-Cl) | H | |
| 3.87 | CH₃ | 4-C₆H₄—OnC₃H₇ | CH₃ | Oil |
| 3.88 | CH₃ | 4-C₆H₄—OCH₂C₆H₄CF₃(3') | CH₃ | 104–106° C. |
| 3.89 | CH₃ | 4-C₆H₄-OisoC₃H₇ | CH₃ | Oil |
| 3.90 | CH₃ | 4-C₆H₄—OC₂H₅ | CH₃ | 142–145° C. |
| 3.91 | CH₃ | —C₆H₃F₂(2,4) | CH₃ | 168–171° C. |
| 3.92 | CH₃ | 4-C₆H₄-OnC₄H₉ | CH₃ | Oil |
| 3.93 | CH₃ | —C₆H₃(CH₃)₂(2,4) | CH₃ | |
| 3.94 | CH₃ | —C₆H₃(CH₃)₂(2,3) | CH₃ | |
| 3.95 | CH₃ | —C₆H₃(CH₃)₂(2,5) | CH₃ | |
| 3.96 | CH₃ | —C₆H₃(CH₃)(2),F(4) | CH₃ | |
| 3.97 | CH₃ | —C₆H₃CH₃(2),F(5) | CH₃ | |
| 3.98 | CH₃ | 4-C₆H₄—O—C₆H₄CF₃(3) | CH₃ | |
| 3.99 | CH₃ | 4-C₆H₄—O—C₆H₄Cl(4) | CH₃ | |
| 3.100 | CH₃ | 4-C₆H₄—O-Allyl | CH₃ | |
| 3.101 | CH₃ | 4-C₆H₄—OCF₃ | CH₃ | |
| 3.102 | CH₃ | 4-C₆H₄—OCH₂Si(CH₃)₃ | CH₃ | |
| 3.103 | CH₃ | 4-C₆H₄—OCH₃ | CH₃ | |
| 3.104 | CH₃ | 4-C₆H₄-Osec.C₄H₉ | CH₃ | |
| 3.105 | CH₃ | 4-C₆H₄-OisoC₄H₉ | CH₃ | |
| 3.106 | CH₃ | 4-C₆H₄—OCH=CCl₂ | CH₃ | |
| 3.107 | CH₃ | 4-C₆H₄—ON=C(CH₃)₂ | CH₃ | |
| 3.108 | CH₃ | 4-C₆H₄—O-Cyclopentyl | CH₃ | |
| 3.109 | CH₃ | —C₆H₃F(2)-OnC₃H₇(4) | CH₃ | |
| 3.110 | CH₃ | —C₆H₃F(2)-OC₂H₅(4) | CH₃ | |
| 3.111 | CH₃ | —C₆H₃(2)-OisoC₃H₇(4) | CH₃ | |
| 3.112 | CH₃ | —C₆H₃F(2)-OCH₃(4) | CH₃ | |
| 3.113 | CH₃ | 3-fluoro-4-methylphenyl-O-CH₂-(1,1-dichlorocyclopropyl) | CH₃ | |
| 3.114 | CH₃ | —C₆H₃OCH₃(2)F(4) | CH₃ | |
| 3.115 | CH₃ | —C₆H₃OCH₃(2)CH₃(4) | CH₃ | |

TABLE 3-continued

[Structure: 4-{2-[(methoxyimino)methyl with R groups]benzyl}-2-methyl-5-methoxy-2,4-dihydro-3H-1,2,4-triazol-3-one]

| Comp. No. | R₁ | R₂ | R₃ | Phys. Data m.p. |
|---|---|---|---|---|
| 3.116 | CH₃ | —C₆H₃CH₃(2)-OCH₃(4) | CH₃ | |
| 3.117 | CH₃ | —C₆H₃CH₃(2)-OC₂H₅(4) | CH₃ | |
| 3.118 | CH₃ | —C₆H₃CH₃(2)-OnC₃H₇(4) | CH₃ | |
| 3.119 | CH₃ | —C₆H₃CH₃(2)-OisoC₃H₇(4) | CH₃ | |
| 3.120 | CH₃ | —C₆H₄-OnC₃H₇(4) | CH₂CH₃ | |
| 3.121 | CH₃ | —C₆H₄—OC₂H₅(4) | CH₂CH₃ | |
| 3.122 | CH₃ | —C₆H₄-OnC₃H₇(4) | CH₂F | |
| 3.123 | CH₃ | —C₆H₄-OnC₃H₇(4) | CH₂—C≡CH | |
| 3.124 | CH₃ | —C₆H₄-OnC₃H₇(4) | (CH₂)₂CH₃ | |
| 3.125 | CH₃ | —C₆H₄-OnC₃H₇(4) | CH(CH₃)₂ | |
| 3.126 | CH₃ | —C₆H₄-OnC₃H₇(4) | CH₂—CH=CH₂ | |
| 3.127 | CH₃ | 2-Tolyl | CH₂CH₃ | |
| 3.128 | CH₃ | —C₆H₃F(2)CH₃(4) | CH₃ | |
| 3.129 | CH₃ | —C₆H₃F(2)CH₃(5) | CH₃ | |
| 3.130 | CH₃ | —C₆H₃F₂(2,5) | CH₃ | |
| 3.131 | CH₃ | —C₆H₄—OCH₂CF₃(4) | CH₃ | |
| 3.132 | CH₃ | —C₆H₄C₂H₅(4) | CH₃ | |
| 3.133 | CH₃ | —COOCH₂CH=CH₂ | CH₃ | |
| 3.134 | CH₃ | —C₆H₄—OCHF₂(4) | CH₃ | |
| 3.135 | CH₃ | 4-C₆H₄—O—C₆H₄F(4') | CH₃ | |
| 3.136 | CH₃ | —COOCH(CH₃)₂ | CH₃ | |
| 3.137 | CH₃ | —C₆H₄Br(4) | CH₃ | |
| 3.138 | CH₃ | 2-Pyridyl | CH₃ | |
| 3.139 | CH₃ | 3-Pyridyl | CH₃ | |
| 3.140 | CH₃ | 4-Pyridyl | CH₃ | |
| 3.141 | CH₃ | 2-Pyrazinyl | CH₃ | |
| 3.142 | CH₃ | 5,6-Dichloropyridinyl(3) | CH₃ | |
| 3.143 | CH₃ | CH₃ | CF₂CHF₂ | |
| 3.144 | CH₃ | 2-Fluoro-4-(4'-fluorobenzyloxy)phenyl | CH₃ | |
| 3.145 | CH₃ | 4-C₆H₄—O—C₆H₄Br(3') | CH₃ | |
| 3.146 | CH₃ | —C₆H₅ | CH₂C≡CH | |

TABLE 4

[Structure: thione analog with H₃CO-triazole-thione-N-benzyl-O-N=C(R₁)-C(R₂)=N-O-R₃]

| Comp. No. | R₁ | R₂ | R₃ | Phys. Data m.p. |
|---|---|---|---|---|
| 4.1 | CH₃ | CH₃ | CH₃ | |
| 4.2 | CH₃ | ▷ (cyclopropyl) | CH₃ | |
| 4.3 | CH₃ | H | CH₃ | |

TABLE 4-continued
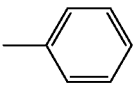
| Comp. No. | R₁ | R₂ | R₃ | Phys. Data m.p. |
|---|---|---|---|---|
| 4.4 | CH₃ | 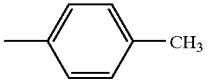 | CH₃ | |
| 4.5 | CH₃ | 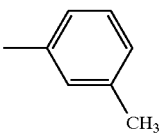 | CH₃ | |
| 4.6 | CH₃ | 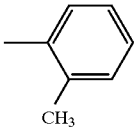 | CH₃ | |
| 4.7 | CH₃ |  | CH₃ | |
| 4.8 | CH₃ | 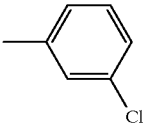 | CH₃ | |
| 4.9 | CH₃ | 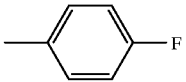 | CH₃ | |
| 4.10 | CH₃ | 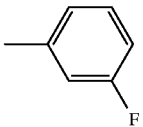 | CH₃ | |
| 4.11 | CH₃ |  | CH₃ | |

TABLE 4-continued
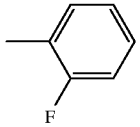
| Comp. No. | R₁ | R₂ | R₃ | Phys. Data m.p. |
|---|---|---|---|---|
| 4.12 | CH₃ | 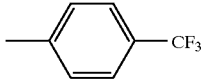 | CH₃ | |
| 4.13 | CH₃ | 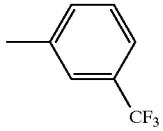 | CH₃ | Oil |
| 4.14 | CH₃ | 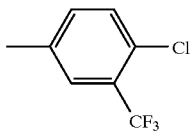 | CH₃ | |
| 4.15 | CH₃ | 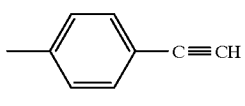 | CH₃ | |
| 4.16 | CH₃ | 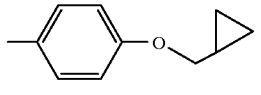 | CH₃ | |
| 4.17 | CH₃ | 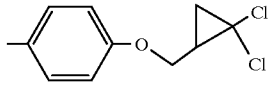 | CH₃ | |
| 4.18 | CH₃ | 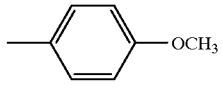 | CH₃ | |
| 4.19 | CH₃ | —⟨C₆H₄⟩—OCH₃ | CH₃ | |

TABLE 4-continued
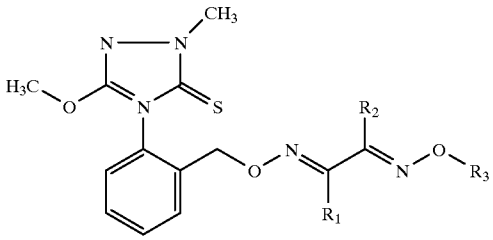
| Comp. No. | R₁ | R₂ | R₃ | Phys. Data m.p. |
|---|---|---|---|---|
| 4.20 | CH₃ | 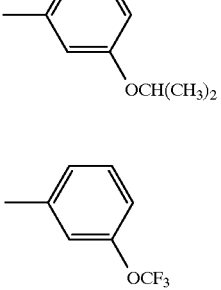 | CH₃ | |
| 4.21 | CH₃ | 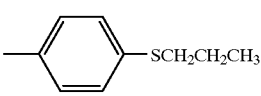 | CH₃ | |
| 4.22 | CH₃ | 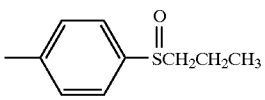 | CH₃ | |
| 4.23 | CH₃ | 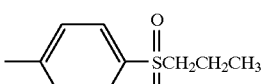 | CH₃ | |
| 4.24 | CH₃ | 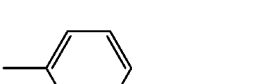 | CH₃ | |
| 4.25 | CH₃ | 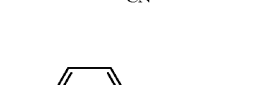 | CH₃ | |
| 4.26 | CH₃ | 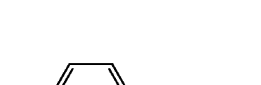 | CH₃ | |
| 4.27 | CH₃ |  | CH₃ | |

TABLE 4-continued
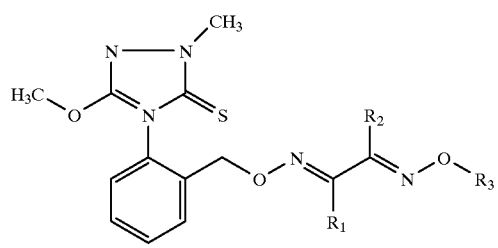
| Comp. No. | R₁ | R₂ | R₃ | Phys. Data m.p. |
|---|---|---|---|---|
| 4.28 | CH₃ | 1-naphthyl | CH₃ | |
| 4.29 | CH₃ | 4-biphenyl | CH₃ | |
| 4.30 | CH₃ | 4'-chloro-4-biphenyl | CH₃ | |
| 4.31 | CH₃ | 4-phenoxyphenyl | CH₃ | |
| 4.32 | CH₃ | 4-(3-chlorophenylthio)phenyl | CH₃ | |
| 4.33 | CH₃ | 4-(3-methylisoxazol-5-yl)phenyl | CH₃ | |
| 4.34 | CH₃ | CN | CH₃ | |
| 4.35 | CH₃ | COOCH₃ | CH₃ | |
| 4.36 | CH₃ | SCH₃ | CH₃ | |
| 4.37 | CH₃ | S(O)CH₃ | CH₃ | |
| 4.38 | CH₃ | S(O)₂CH₃ | CH₃ | |
| 4.39 | CH₃ | O(CH₂)₄CH₃ | CH₃ | |
| 4.40 | CH₃ | O-phenyl | CH₃ | |

TABLE 4-continued

[Structure: 3-methoxy-4-(2-substituted-phenyl)-2-methyl-2,4-dihydro-[1,2,4]triazole-3-thione with CH$_2$-O-N=C(R$_1$)-C(R$_2$)=N-O-R$_3$ side chain]

| Comp. No. | R$_1$ | R$_2$ | R$_3$ | Phys. Data m.p. |
|---|---|---|---|---|
| 4.41 | CH$_3$ | O-C$_6$H$_4$-4-Cl | CH$_3$ | |
| 4.42 | CH$_3$ | O-C$_6$H$_4$-3-Cl | CH$_3$ | |
| 4.43 | CH$_3$ | O-C$_6$H$_4$-4-CF$_3$ | CH$_3$ | |
| 4.44 | CH$_3$ | O-C$_6$H$_4$-3-CF$_3$ | CH$_3$ | |
| 4.45 | CH$_3$ | O-(pyridin-2-yl) | CH$_3$ | |
| 4.46 | CH$_3$ | O-(pyridin-3-yl) | CH$_3$ | |
| 4.47 | CH$_3$ | O-(pyridin-4-yl) | CH$_3$ | |
| 4.48 | CH$_3$ | 2-(4,5-dihydrothiazol-2-yl) | CH$_3$ | |

TABLE 4-continued

[Structure: 3-methoxy-1-methyl-4-(2-(((R1)C=N-O-CH2)phenyl)-1H-1,2,4-triazole-5(4H)-thione with =N-O-R3 on R2-substituted carbon]

| Comp. No. | R₁ | R₂ | R₃ | Phys. Data m.p. |
|---|---|---|---|---|
| 4.49 | CH₃ | 2,4,4-trimethyl-4,5-dihydrooxazol-2-yl (attached via position) | CH₃ | |
| 4.50 | CH₃ | CH₂–C₆H₅ | CH₃ | |
| 4.51 | CH₃ | CH₂–C₆H₄–OCH₃ (para) | CH₃ | |
| 4.52 | CH₃ | CH₂–C₆H₄–CF₃ (para) | CH₃ | |
| 4.53 | CH₃ | CH₂–C₆H₄–CF₃ (meta) | CH₃ | |
| 4.54 | CH₃ | CH₂–C₆H₄–Cl (para) | CH₃ | |
| 4.55 | CH₃ | CH₂–C₆H₄–Cl (meta) | CH₃ | |
| 4.56 | CH₃ | CH₂–C₆H₄–Cl (ortho) | CH₃ | |

TABLE 4-continued

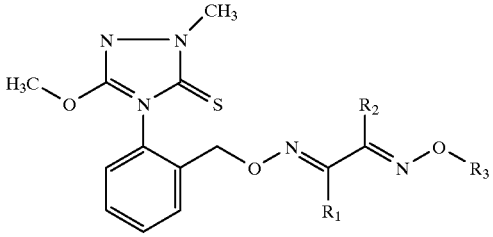

| Comp. No. | $R_1$ | $R_2$ | $R_3$ | Phys. Data m.p. |
|---|---|---|---|---|
| 4.57 | $CH_3$ | 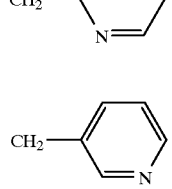 | $CH_3$ | |
| 4.58 | $CH_3$ | 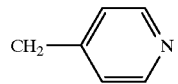 | $CH_3$ | |
| 4.59 | $CH_3$ |  | $CH_3$ | |
| 4.60 | H | $CH_3$ | $CH_3$ | |
| 4.61 | 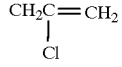 | $CH_3$ | $CH_3$ | |
| 4.62 | $CH_3CH_2$ | $CH_3$ | $CH_3$ | |
| 4.63 | $CH_3$ | $CH_3$ | $CH_2CH_3$ | |
| 4.64 | $CH_3$ | $CH_3$ | $CH_2CH_2CH_3$ | |
| 4.65 | $CH_3$ | $CH_3$ | $(CH_2)_3CH_3$ | |
| 4.66 | $CH_3$ | $CH_3$ | $(CH_2)_4CH_3$ | |
| 4.67 | $CH_3$ | $CH_3$ | $(CH_2)_5CH_3$ | |
| 4.68 | $CH_3$ | $CH_3$ | $CH_2C(CH_3)_3$ | |
| 4.69 | $CH_3$ | $CH_3$ | $CH_2F$ | |
| 4.70 | $CH_3$ | $CH_3$ | $CH_2CF_3$ | |
| 4.71 | $CH_3$ | $CH_3$ | $CH_2CH_2F$ | |
| 4.72 | $CH_3$ | $CH_3$ | $CH_2CH_2CH_2CF_3$ | |
| 4.73 | $CH_3$ | $CH_3$ | $CH_2OCH_3$ | |
| 4.74 | $CH_3$ | $CH_3$ | $CH_2C(Cl)=CH_2$ | |
| 4.75 | $CH_3$ | $CH_3$ | 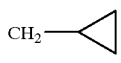 | |
| 4.76 | $CH_3$ | $CH_3$ | $CH_2C\equiv CH$ | |
| 4.77 | H | $CH_3$ | $CH_3$ | |
| 4.78 | H | H | 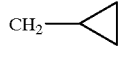 | |
| 4.79 | H | H | $CH_3$ | |
| 4.80 | $CH_3$ | $CH_3$ | H | |
| 4.81 | $C_2H_5$ | $CH_3$ | H | |
| 4.82 | $CH_3$ | —$C_6H_5$ | H | |
| 4.83 | $CH_3$ | —$CH_2$—O—$CH_3$ | H | |
| 4.84 | $CH_3$ | —$CH_2$—O—$CH_3$ | $CH_3$ | |
| 4.85 | $CH_3$ | —$C_6H_4$—$C_6H_4$(p) | H | |

TABLE 4-continued

[Structure: 5-methoxy-2-methyl-4-(2-(oxyimino-methyl)phenyl)-2,4-dihydro-3H-1,2,4-triazole-3-thione with bis-oxime substituent showing R1, R2, R3 groups]

| Comp. No. | R₁ | R₂ | R₃ | Phys. Data m.p. |
|---|---|---|---|---|
| 4.86 | CH₃ | —C₆H₅(4-Cl) | H | |
| 4.87 | CH₃ | 4-C₆H₄-OnC₃H₇ | CH₃ | |
| 4.88 | CH₃ | 4-C₆H₄—OCH₂C₆H₄CF₃(3') | CH₃ | |
| 4.89 | CH₃ | 4-C₆H₄-OisoC₃H₇ | CH₃ | |
| 4.90 | CH₃ | 4-C₆H₄—OC₂H₅ | CH₃ | |
| 4.91 | CH₃ | —C₆H₃F₂(2,4) | CH₃ | |
| 4.92 | CH₃ | 4-C₆H₄-OnC₄H₉ | CH₃ | |
| 4.93 | CH₃ | —C₆H₃(CH₃)₂(2,4) | CH₃ | |
| 4.94 | CH₃ | —C₆H₃(CH₃)₂(2,3) | CH₃ | |
| 4.95 | CH₃ | —C₆H₃(CH₃)₂(2,5) | CH₃ | |
| 4.96 | CH₃ | —C₆H₃CH₃(2),F(4) | CH₃ | |
| 4.97 | CH₃ | —C₆H₃CH₃(2),F(5) | CH₃ | |
| 4.98 | CH₃ | 4-C₆H₄—O—C₆H₄CF₃(3) | CH₃ | |
| 4.99 | CH₃ | 4-C₆H₄—O—C₆H₄Cl(4) | CH₃ | |
| 4.100 | CH₃ | 4-C₆H₄—O-Allyl | CH₃ | |
| 4.101 | CH₃ | 4-C₆H₄—OCF₃ | CH₃ | |
| 4.102 | CH₃ | 4-C₆H₄—OCH₂Si(CH₃)₃ | CH₃ | |
| 4.103 | CH₃ | 4-C₆H₄—OCH₃ | CH₃ | |
| 4.104 | CH₃ | 4-C₆H₄-Osec.C₄H₉ | CH₃ | |
| 4.105 | CH₃ | 4-C₆H₄-OisoC₄H₉ | CH₃ | |
| 4.106 | CH₃ | 4-C₆H₄—OCH=CCl₂ | CH₃ | |
| 4.107 | CH₃ | 4-C₆H₄—ON=C(CH₃)₂ | CH₃ | |
| 4.108 | CH₃ | 4-C₆H₄—O-Cyclopentyl | CH₃ | |
| 4.109 | CH₃ | —C₆H₃F(2)-OnC₃H₇(4) | CH₃ | |
| 4.110 | CH₃ | —C₆H₃F(2)-OC₂H₅(4) | CH₃ | |
| 4.111 | CH₃ | —C₆H₃F(2)-OisoC₃H₇(4) | CH₃ | |
| 4.112 | CH₃ | —C₆H₃F(2)-OCH₃(4) | CH₃ | |
| 4.113 | CH₃ | [structure: 3-fluoro-4-methylphenyl-O-CH₂-cyclopropyl with 2,2-dichloro] | CH₃ | |
| 4.114 | CH₃ | —C₆H₃OCH₃(2)F(4) | CH₃ | |
| 4.115 | CH₃ | —C₆H₃OCH₃(2)CH₃(4) | CH₃ | |
| 4.116 | CH₃ | —C₆H₃CH₃(2)-OCH₃(4) | CH₃ | |
| 4.117 | CH₃ | —C₆H₃CH₃(2)-OC₂H₅(4) | CH₃ | |
| 4.118 | CH₃ | —C₆H₃CH₃(2)-OnC₃H₇(4) | CH₃ | |
| 4.119 | CH₃ | —C₆H₃CH₃(2)-OisoC₃H₇(4) | CH₃ | |
| 4.120 | CH₃ | —C₆H₄-OnC₃H₇(4) | CH₂CH₃ | |
| 4.121 | CH₃ | —C₆H₄—OC₂H₅(4) | CH₂CH₃ | |
| 4.122 | CH₃ | —C₆H₄-OnC₃H₇(4) | CH₂F | |
| 4.123 | CH₃ | —C₆H₄-OnC₃H₇(4) | CH₂—C≡CH | |
| 4.124 | CH₃ | —C₆H₄-OnC₃H₇(4) | (CH₂)₂CH₃ | |
| 4.125 | CH₃ | —C₆H₄-OnC₃H₇(4) | CH(CH₃)₂ | |
| 4.126 | CH₃ | —C₆H₄-OnC₃H₇(4) | CH₂—CH=CH₂ | |
| 4.127 | CH₃ | 2-Tolyl | CH₂CH₃ | |
| 4.128 | CH₃ | —C₆H₃F(2)CH₃(4) | CH₃ | |
| 4.129 | CH₃ | —C₆H₃F(2)CH₃(5) | CH₃ | |
| 4.130 | CH₃ | —C₆H₃F₂(2,5) | CH₃ | |
| 4.131 | CH₃ | —C₆H₄—OCH₂CF₃(4) | CH₃ | |
| 4.132 | CH₃ | —C₆H₄C₂H₅(4) | CH₃ | |
| 4.133 | CH₃ | —COOCH₂CH=CH₂ | CH₃ | |
| 4.134 | CH₃ | —C₆H₄—OCHF₂(4) | CH₃ | |
| 4.135 | CH₃ | 4-C₆H₄—O—C₆H₄F(4') | CH₃ | |
| 4.136 | CH₃ | —COOCH(CH₃)₂ | CH₃ | |
| 4.137 | CH₃ | —C₆H₄Br(4) | CH₃ | |
| 4.138 | CH₃ | 2-Pyridyl | CH₃ | |
| 4.139 | CH₃ | 3-Pyridyl | CH₃ | |
| 4.140 | CH₃ | 4-Pyridyl | CH₃ | |

TABLE 4-continued
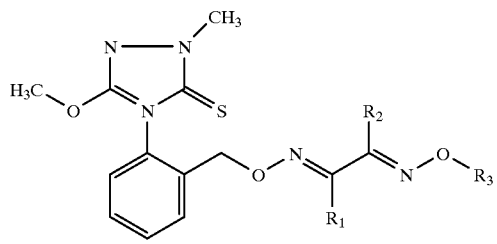
| Comp. No. | R₁ | R₂ | R₃ | Phys. Data m.p. |
|---|---|---|---|---|
| 4.141 | CH₃ | 2-Pyrazinyl | CH₃ | |
| 4.142 | CH₃ | 5,6-Dichloropyridinyl(3) | CH₃ | |
| 4.143 | CH₃ | CH₃ | CF₂CHF₂ | |
| 4.144 | CH₃ | 2-Fluoro-4-(4'-fluorobenzyloxy)phenyl | CH₃ | |
| 4.145 | CH₃ | 4-C₆H₄—O—C₆H₄Br(3') | CH₃ | |
| 4.146 | CH₃ | —C₆H₅ | CH₂C≡CH | |
TABLE 5
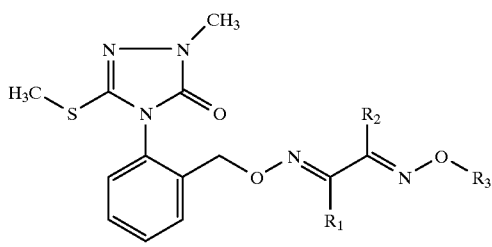
| Comp. No. | R₁ | R₂ | R₃ | Phys. Content m.p. |
|---|---|---|---|---|
| 5.1 | CH₃ | CH₃ | CH₃ | |
| 5.2 | CH₃ | △ | CH₃ | |
| 5.3 | CH₃ | H | CH₃ | |
| 5.4 | CH₃ | ⌬ | CH₃ | |
| 5.5 | CH₃ | 4-CH₃-C₆H₄ | CH₃ | |
| 5.6 | CH₃ | 3-CH₃-C₆H₄ | CH₃ | |

TABLE 5-continued
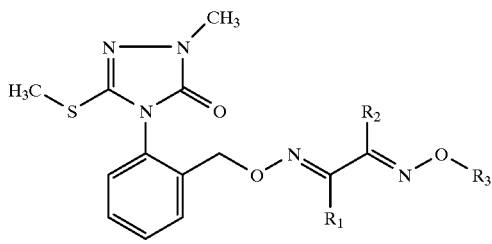
| Comp. No. | R₁ | R₂ | R₃ | Phys. Content m.p. |
|---|---|---|---|---|
| 5.7 | CH₃ | 2,3-dimethylphenyl | CH₃ | |
| 5.8 | CH₃ | 4-chlorophenyl | CH₃ | |
| 5.9 | CH₃ | 3-chlorophenyl | CH₃ | |
| 5.10 | CH₃ | 4-fluorophenyl | CH₃ | |
| 5.11 | CH₃ | 3-fluorophenyl | CH₃ | |
| 5.12 | CH₃ | 2,3-difluorophenyl | CH₃ | |
| 5.13 | CH₃ | 4-trifluoromethylphenyl | CH₃ | |
| 5.14 | CH₃ | 3-trifluoromethylphenyl | CH₃ | |

TABLE 5-continued

[Structure: 2-methyl-5-(methylthio)-4-[2-(oxime ether)phenyl]-2,4-dihydro-3H-1,2,4-triazol-3-one with bis-oxime linker bearing R₁, R₂, and OR₃ groups]

| Comp. No. | R₁ | R₂ | R₃ | Phys. Content m.p. |
|---|---|---|---|---|
| 5.15 | CH₃ | 4-Cl-3-CF₃-phenyl | CH₃ | |
| 5.16 | CH₃ | 4-(C≡CH)-phenyl | CH₃ | |
| 5.17 | CH₃ | 4-(OCH₂-cyclopropyl)-phenyl | CH₃ | |
| 5.18 | CH₃ | 4-(OCH₂-(2,2-dichlorocyclopropyl))-phenyl | CH₃ | |
| 5.19 | CH₃ | 4-OCH₃-phenyl | CH₃ | |
| 5.20 | CH₃ | 3-OCH(CH₃)₂-phenyl | CH₃ | |
| 5.21 | CH₃ | 3-OCF₃-phenyl | CH₃ | |
| 5.22 | CH₃ | 4-SCH₂CH₂CH₃-phenyl | CH₃ | |

TABLE 5-continued
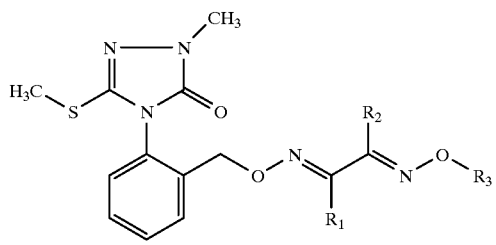
| Comp. No. | R₁ | R₂ | R₃ | Phys. Content m.p. |
|---|---|---|---|---|
| 5.23 | CH₃ | 4-(CH₃CH₂CH₂S(O)-)phenyl | CH₃ | |
| 5.24 | CH₃ | 4-(CH₃CH₂CH₂S(O)₂-)phenyl | CH₃ | |
| 5.25 | CH₃ | 3-cyanophenyl | CH₃ | |
| 5.26 | CH₃ | 4-nitrophenyl | CH₃ | |
| 5.27 | CH₃ | 2-naphthyl | CH₃ | |
| 5.28 | CH₃ | 4-quinolinyl | CH₃ | |
| 5.29 | CH₃ | 4-biphenyl | CH₃ | |
| 5.30 | CH₃ | 4'-chloro-4-biphenyl | CH₃ | |

TABLE 5-continued
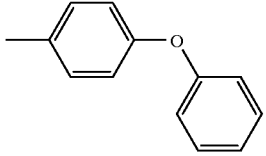
| Comp. No. | R₁ | R₂ | R₃ | Phys. Content m.p. |
|---|---|---|---|---|
| 5.31 | CH₃ | 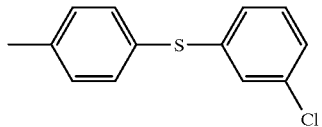 | CH₃ | |
| 5.32 | CH₃ | 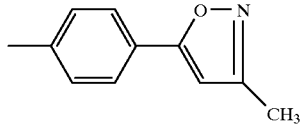 | CH₃ | |
| 5.33 | CH₃ | 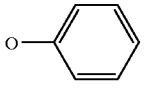 | CH₃ | |
| 5.34 | CH₃ | CN | CH₃ | |
| 5.35 | CH₃ | COOCH₃ | CH₃ | |
| 5.36 | CH₃ | SCH₃ | CH₃ | |
| 5.37 | CH₃ | S(O)CH₃ | CH₃ | |
| 5.38 | CH₃ | S(O)₂CH₃ | CH₃ | |
| 5.39 | CH₃ | O(CH₂)₄CH₃ | CH₃ | |
| 5.40 | CH₃ | 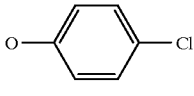 | CH₃ | |
| 5.41 | CH₃ | 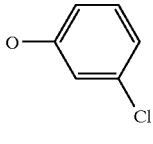 | CH₃ | |
| 5.42 | CH₃ | 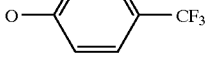 | CH₃ | |
| 5.43 | CH₃ |  | CH₃ | |

TABLE 5-continued

[Structure: 2-methyl-5-(methylthio)-4-[2-(substituted)phenyl]-2,4-dihydro-3H-1,2,4-triazol-3-one derivative with -CH₂-O-N=C(R₁)-C(R₂)=N-O-R₃ side chain]

| Comp. No. | R₁ | R₂ | R₃ | Phys. Content m.p. |
|---|---|---|---|---|
| 5.44 | CH₃ | O—(3-CF₃-phenyl) | CH₃ | |
| 5.45 | CH₃ | O—(2-pyridyl) | CH₃ | |
| 5.46 | CH₃ | O—(3-pyridyl) | CH₃ | |
| 5.47 | CH₃ | O—(4-pyridyl) | CH₃ | |
| 5.48 | CH₃ | 2-(4,5-dihydrothiazolyl) | CH₃ | |
| 5.49 | CH₃ | 2-(4,4-dimethyl-4,5-dihydrooxazolyl) | CH₃ | |
| 5.50 | CH₃ | CH₂—phenyl | CH₃ | |
| 5.51 | CH₃ | CH₂—(4-OCH₃-phenyl) | CH₃ | |
| 5.52 | CH₃ | CH₂—(4-CF₃-phenyl) | CH₃ | |

TABLE 5-continued
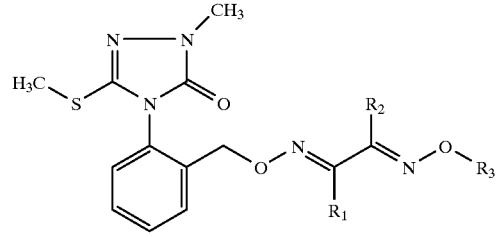
| Comp. No. | R₁ | R₂ | R₃ | Phys. Content m.p. |
|---|---|---|---|---|
| 5.53 | CH₃ | 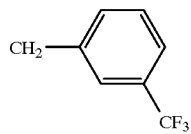 | CH₃ | |
| 5.54 | CH₃ | 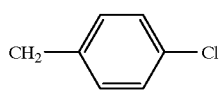 | CH₃ | |
| 5.55 | CH₃ | 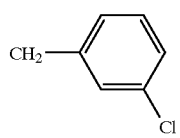 | CH₃ | |
| 5.56 | CH₃ | 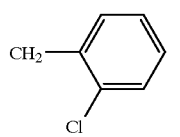 | CH₃ | |
| 5.57 | CH₃ | 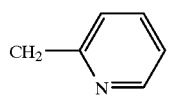 | CH₃ | |
| 5.58 | CH₃ | 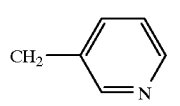 | CH₃ | |
| 5.59 | CH₃ | 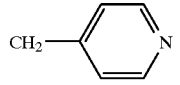 | CH₃ | |
| 5.60 | H | CH₃ | CH₃ | |
| 5.61 |  | CH₃ | CH₃ | |
| 5.62 | CH₃CH₂ | CH₃ | CH₃ | |
| 5.63 | CH₃ | CH₃ | CH₂CH₃ | |
| 5.64 | CH₃ | CH₃ | CH₂CH₂CH₃ | |
| 5.65 | CH₃ | CH₃ | (CH₂)₃CH₃ | |
| 5.66 | CH₃ | CH₃ | (CH₂)₄CH₃ | |

TABLE 5-continued

| Comp. No. | R₁ | R₂ | R₃ | Phys. Content m.p. |
|---|---|---|---|---|
| 5.67 | CH₃ | CH₃ | (CH₂)₅CH₃ | |
| 5.68 | CH₃ | CH₃ | CH₂C(CH₃)₂ | |
| 5.69 | CH₃ | CH₃ | CH₂F | |
| 5.70 | CH₃ | CH₃ | CH₂CF₃ | |
| 5.71 | CH₃ | CH₃ | CH₂CH₂F | |
| 5.72 | CH₃ | CH₃ | CH₂CH₂CH₂CF₃ | |
| 5.73 | CH₃ | CH₃ | CH₂OCH₃ | |
| 5.74 | CH₃ | CH₃ | CH₂C(Cl)=CH₂ | |
| 5.75 | CH₃ | CH₃ | CH₂-cyclopropyl | |
| 5.76 | CH₃ | CH₃ | CH₂C≡CH | |
| 5.77 | H | CH₃ | CH₃ | |
| 5.78 | H | H | CH₂-cyclopropyl | |
| 5.79 | H | H | CH₃ | |
| 5.80 | CH₃ | CH₃ | H | |
| 5.81 | C₂H₅ | CH₃ | H | |
| 5.82 | CH₃ | —C₆H₅ | H | |
| 5.83 | CH₃ | —CH₂—O—CH₃ | H | |
| 5.84 | CH₃ | —CH₂—O—CH₃ | CH₃ | |
| 5.85 | CH₃ | —C₆H₄—C₆H₅(p) | H | |
| 5.86 | CH₃ | —C₆H₅(4-Cl) | H | |
| 5.87 | CH₃ | 4-C₆H₄-OnC₃H₇ | CH₃ | Oil |
| 5.88 | CH₃ | 4-C₆H₄—OCH₂C₆H₄CF₃(3') | CH₃ | |
| 5.89 | CH₃ | 4-C₆H₄-OisoC₃H₇ | CH₃ | |
| 5.90 | CH₃ | 4-C₆H₄—OC₂H₅ | CH₃ | |
| 5.91 | CH₃ | —C₆H₃F₂(2,4) | CH₃ | 145–147° C. |
| 5.92 | CH₃ | 4-C₆H₄-OnC₄H₉ | CH₃ | |
| 5.93 | CH₃ | —C₆H₃(CH₃)₂(2,4) | CH₃ | |
| 5.94 | CH₃ | —C₆H₃(CH₃)₂(2,3) | CH₃ | |
| 5.95 | CH₃ | —C₆H₃(CH₃)₂(2,5) | CH₃ | |
| 5.96 | CH₃ | —C₆H₃CH₃(2),F(4) | CH₃ | |
| 5.97 | CH₃ | —C₆H₃CH₃(2),F(5) | CH₃ | |
| 5.98 | CH₃ | 4-C₆H₄—O—C₆H₄CF₃(3) | CH₃ | |
| 5.99 | CH₃ | 4-C₆H₄—O—C₆H₄Cl(4) | CH₃ | |
| 5.100 | CH₃ | 4-C₆H₄—O-Allyl | CH₃ | |
| 5.101 | CH₃ | 4-C₆H₄—OCF₃ | CH₃ | |
| 5.102 | CH₃ | 4-C₆H₄—OCH₂Si(CH₃)₃ | CH₃ | |
| 5.103 | CH₃ | 4-C₆H₄—OCH₃ | CH₃ | |
| 5.104 | CH₃ | 4-C₆H₄-Osec.C₄H₉ | CH₃ | |
| 5.105 | CH₃ | 4-C₆H₄-OisoC₄H₉ | CH₃ | |
| 5.106 | CH₃ | 4-C₆H₄—OCH=CCl₂ | CH₃ | |
| 5.107 | CH₃ | 4-C₆H₄—ON=C(CH₃)₂ | CH₃ | |
| 5.108 | CH₃ | 4-C₆H₄—O-Cyclopentyl | CH₃ | |
| 5.109 | CH₃ | —C₆H₃F(2)-OnC₃H₇(4) | CH₃ | |
| 5.110 | CH₃ | —C₆H₃F(2)-OC₂H₅(4) | CH₃ | |
| 5.111 | CH₃ | —C₆H₃F(2)-OisoC₃H₇(4) | CH₃ | |
| 5.112 | CH₃ | —C₆H₃F(2)-OCH₃(4) | CH₃ | |

TABLE 5-continued

[Structure: 2-methyl-5-(methylthio)-4-[2-(substituted)phenyl]-2,4-dihydro-3H-1,2,4-triazol-3-one with CH₂-O-N=C(R₁)-C(R₂)=N-O-R₃ side chain]

| Comp. No. | R₁ | R₂ | R₃ | Phys. Content m.p. |
|---|---|---|---|---|
| 5.113 | CH₃ | 3-fluoro-4-[(2,2-dichlorocyclopropyl)methoxy]phenyl | CH₃ | |
| 5.114 | CH₃ | —C₆H₃OCH₃(2)F(4) | CH₃ | |
| 5.115 | CH₃ | —C₆H₃OCH₃(2)CH₃(4) | CH₃ | |
| 5.116 | CH₃ | —C₆H₃CH₃(2)-OCH₃(4) | CH₃ | |
| 5.117 | CH₃ | —C₆H₃CH₃(2)-OC₂H₅(4) | CH₃ | |
| 5.118 | CH₃ | —C₆H₃CH₃(2)-OnC₃H₇(4) | CH₃ | |
| 5.119 | CH₃ | —C₆H₃CH₂(2)-OisoC₃H₇(4) | CH₃ | |
| 5.120 | CH₃ | —C₆H₄-OnC₃H₇(4) | CH₂CH₃ | |
| 5.121 | CH₃ | —C₆H₄—OC₂H₅(4) | CH₂CH₃ | |
| 5.122 | CH₃ | —C₆H₄-OnC₃H₇(4) | CH₂F | |
| 5.123 | CH₃ | —C₆H₄-OnC₃H₇(4) | CH₂—C≡CH | |
| 5.124 | CH₃ | —C₆H₄-OnC₃H₇(4) | (CH₂)₂CH₃ | |
| 5.125 | CH₃ | —C₆H₄-OnC₃H₇(4) | CH(CH₃)₂ | |
| 5.126 | CH₃ | —C₆H₄-OnC₃H₇(4) | CH₂—CH=CH₂ | |
| 5.127 | CH₃ | 2-Tolyl | CH₂CH₃ | |
| 5.128 | CH₃ | —C₆H₃F(2)CH₃(4) | CH₃ | |
| 5.129 | CH₃ | —C₆H₃F(2)CH₃(5) | CH₃ | |
| 5.130 | CH₃ | —C₆H₃F₂(2,5) | CH₃ | |
| 5.131 | CH₃ | —C₆H₄—OCH₂CF₃(4) | CH₃ | |
| 5.132 | CH₃ | —C₆H₄C₂H₅(4) | CH₃ | |
| 5.133 | CH₃ | —COOCH₂CH=CH₂ | CH₃ | |
| 5.134 | CH₃ | —C₆H₄—OCHF₂(4) | CH₃ | |
| 5.135 | CH₃ | 4-C₆H₄—O—C₆H₄F(4') | CH₃ | |
| 5.136 | CH₃ | —COOCH(CH₃)₂ | CH₃ | |
| 5.137 | CH₃ | —C₆H₄Br(4) | CH₃ | |
| 5.138 | CH₃ | 2-Pyridyl | CH₃ | |
| 5.139 | CH₃ | 3-Pyridyl | CH₃ | |
| 5.140 | CH₃ | 4-Pyridyl | CH₃ | |
| 5.141 | CH₃ | 2-Pyrazinyl | CH₃ | |
| 5.142 | CH₃ | 5,6-Dichloropyridinyl(3) | CH₃ | |
| 5.143 | CH₃ | CH₃ | CF₂CHF₂ | |
| 5.144 | CH₃ | 2-Fluoro-4-(4'-fluorobenzyloxy)phenyl | CH₃ | |
| 5.145 | CH₃ | 4-C₆H₄—O—C₆H₄Br(3') | CH₃ | |
| 5.146 | CH₃ | —C₆H₅ | CH₂C≡CH | |

TABLE 6
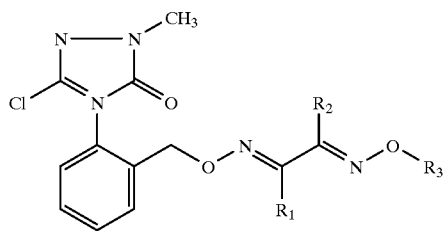
| Comp. No. | R₁ | R₂ | R₃ | Phys. constant m.p. |
|---|---|---|---|---|
| 6.1 | CH₃ | CH₃ | CH₃ | |
| 6.2 | CH₃ | cyclopropyl | CH₃ | |
| 6.3 | CH₃ | H | CH₃ | |
| 6.4 | CH₃ | phenyl | CH₃ | |
| 6.5 | CH₃ | 4-CH₃-phenyl | CH₃ | |
| 6.6 | CH₃ | 3-CH₃-phenyl | CH₃ | |
| 6.7 | CH₃ | 2,3-diCH₃-phenyl | CH₃ | |
| 6.8 | CH₃ | 4-Cl-phenyl | CH₃ | |
| 6.9 | CH₃ | 3-Cl-phenyl | CH₃ | |
| 6.10 | CH₃ | 4-F-phenyl | CH₃ | |

TABLE 6-continued

[Structure: 5-chloro-2-methyl-4-[2-(aminooxymethyl)phenyl]-2,4-dihydro-3H-1,2,4-triazol-3-one with oxime ether side chain bearing R₁, R₂, R₃ substituents]

| Comp. No. | R₁ | R₂ | R₃ | Phys. constant m.p. |
|---|---|---|---|---|
| 6.11 | CH₃ | 3-fluorophenyl | CH₃ | |
| 6.12 | CH₃ | 2-fluorophenyl | CH₃ | |
| 6.13 | CH₃ | 4-(trifluoromethyl)phenyl | CH₃ | |
| 6.14 | CH₃ | 3-(trifluoromethyl)phenyl | CH₃ | |
| 6.15 | CH₃ | 4-chloro-3-(trifluoromethyl)phenyl | CH₃ | |
| 6.16 | CH₃ | 4-ethynylphenyl | CH₃ | |
| 6.17 | CH₃ | 4-(cyclopropylmethoxy)phenyl | CH₃ | |
| 6.18 | CH₃ | 4-[(2,2-dichlorocyclopropyl)methoxy]phenyl | CH₃ | |

TABLE 6-continued

[Structure: 3-chloro-4-[2-(substituted)phenyl]-1-methyl-1H-1,2,4-triazol-5(4H)-one with oxime ether side chain containing R1, R2, R3 substituents]

| Comp. No. | R1 | R2 | R3 | Phys. constant m.p. |
|---|---|---|---|---|
| 6.19 | CH₃ | 4-methoxyphenyl (—C₆H₄—OCH₃) | CH₃ | |
| 6.20 | CH₃ | 3-isopropoxyphenyl (—C₆H₄—OCH(CH₃)₂) | CH₃ | |
| 6.21 | CH₃ | 3-trifluoromethoxyphenyl (—C₆H₄—OCF₃) | CH₃ | |
| 6.22 | CH₃ | 4-(propylthio)phenyl (—C₆H₄—SCH₂CH₂CH₃) | CH₃ | |
| 6.23 | CH₃ | 4-(propylsulfinyl)phenyl (—C₆H₄—S(O)CH₂CH₂CH₃) | CH₃ | |
| 6.24 | CH₃ | 4-(propylsulfonyl)phenyl (—C₆H₄—S(O)₂CH₂CH₂CH₃) | CH₃ | |
| 6.25 | CH₃ | 3-cyanophenyl (—C₆H₄—CN) | CH₃ | |
| 6.26 | CH₃ | 4-nitrophenyl (—C₆H₄—NO₂) | CH₃ | |

TABLE 6-continued
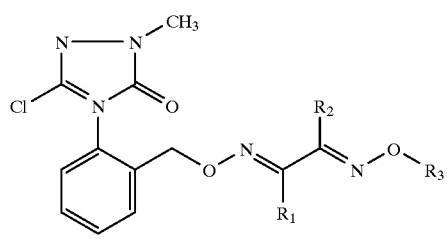
| Comp. No. | R₁ | R₂ | R₃ | Phys. constant m.p. |
|---|---|---|---|---|
| 6.27 | CH₃ | (2-naphthyl) | CH₃ | |
| 6.28 | CH₃ | (1-naphthyl) | CH₃ | |
| 6.29 | CH₃ | (4-biphenyl) | CH₃ | |
| 6.30 | CH₃ | (4'-chloro-4-biphenyl) | CH₃ | |
| 6.31 | CH₃ | (4-phenoxyphenyl) | CH₃ | |
| 6.32 | CH₃ | (4-(3-chlorophenylthio)phenyl) | CH₃ | |
| 6.33 | CH₃ | (4-(3-methylisoxazol-5-yl)phenyl) | CH₃ | |
| 6.34 | CH₃ | CN | CH₃ | |
| 6.35 | CH₃ | COOCH₃ | CH₃ | |
| 6.36 | CH₃ | SCH₃ | CH₃ | |
| 6.37 | CH₃ | S(O)CH₃ | CH₃ | |
| 6.38 | CH₃ | S(O)₂CH₃ | CH₃ | |

TABLE 6-continued
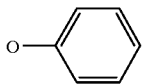
| Comp. No. | $R_1$ | $R_2$ | $R_3$ | Phys. constant m.p. |
|---|---|---|---|---|
| 6.39 | $CH_3$ | $O(CH_2)_4CH_3$ | $CH_3$ | |
| 6.40 | $CH_3$ | 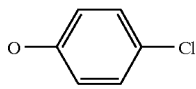 | $CH_3$ | |
| 6.41 | $CH_3$ | 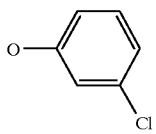 | $CH_3$ | |
| 6.42 | $CH_3$ | 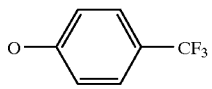 | $CH_3$ | |
| 6.43 | $CH_3$ | 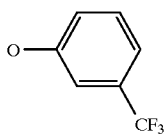 | $CH_3$ | |
| 6.44 | $CH_3$ | 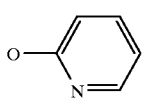 | $CH_3$ | |
| 6.45 | $CH_3$ | 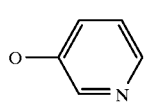 | $CH_3$ | |
| 6.46 | $CH_3$ | 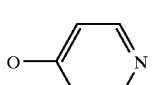 | $CH_3$ | |
| 6.47 | $CH_3$ |  | $CH_3$ | |

TABLE 6-continued
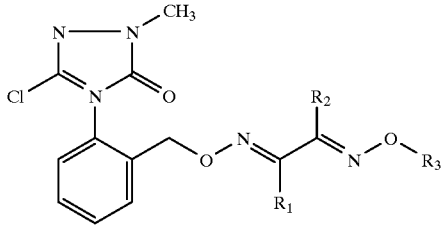
| Comp. No. | R₁ | R₂ | R₃ | Phys. constant m.p. |
|---|---|---|---|---|
| 6.48 | CH₃ | 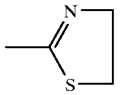 | CH₃ | |
| 6.49 | CH₃ | 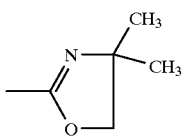 | CH₃ | |
| 6.50 | CH₃ | 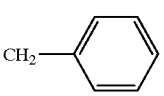 | CH₃ | |
| 6.51 | CH₃ | 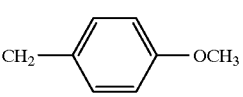 | CH₃ | |
| 6.52 | CH₃ | 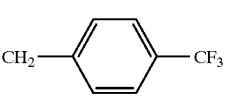 | CH₃ | |
| 6.53 | CH₃ | 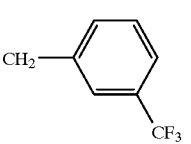 | CH₃ | |
| 6.54 | CH₃ | 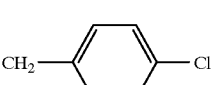 | CH₃ | |
| 6.55 | CH₃ | 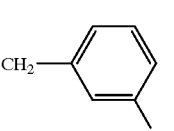 | CH₃ | |

TABLE 6-continued

[Structure: 3-chloro-1-methyl-4-[2-(oximino ether-CH₂O-N=C(R₁)-C(R₂)=N-O-R₃)phenyl]-1,2,4-triazol-5(4H)-one]

| Comp. No. | R₁ | R₂ | R₃ | Phys. constant m.p. |
|---|---|---|---|---|
| 6.56 | CH₃ | CH₂-(2-chlorophenyl) | CH₃ | |
| 6.57 | CH₃ | CH₂-(2-pyridyl) | CH₃ | |
| 6.58 | CH₃ | CH₂-(3-pyridyl) | CH₃ | |
| 6.59 | CH₃ | CH₂-(4-pyridyl) | CH₃ | |
| 6.60 | H | CH₃ | CH₃ | |
| 6.61 | cyclopropyl | CH₃ | CH₃ | |
| 6.62 | CH₃CH₂ | CH₃ | CH₃ | |
| 6.63 | CH₃ | CH₃ | CH₂CH₃ | |
| 6.64 | CH₃ | CH₃ | CH₂CH₂CH₃ | |
| 6.65 | CH₃ | CH₃ | (CH₂)₃CH₃ | |
| 6.66 | CH₃ | CH₃ | (CH₂)₄CH₃ | |
| 6.67 | CH₃ | CH₃ | (CH₂)₅CH₃ | |
| 6.68 | CH₃ | CH₃ | CH₂C(CH₃)₃ | |
| 6.69 | CH₃ | CH₃ | CH₂F | |
| 6.70 | CH₃ | CH₃ | CH₂CF₃ | |
| 6.71 | CH₃ | CH₃ | CH₂CH₂F | |
| 6.72 | CH₃ | CH₃ | CH₂CH₂CH₂CF₃ | |
| 6.73 | CH₃ | CH₃ | CH₂OCH₃ | |
| 6.74 | CH₃ | CH₃ | CH₂C(Cl)=CH₂ | |
| 6.75 | CH₃ | CH₃ | CH₂-cyclopropyl | |
| 6.76 | CH₃ | CH₃ | CH₂C≡CH | |
| 6.77 | H | CH₃ | CH₃ | |

TABLE 6-continued

[Structure: 5-chloro-4-{2-[(oxyimino)methyl]phenyl}-2-methyl-2,4-dihydro-3H-1,2,4-triazol-3-one with bis-oxime ether side chain containing R1, R2, R3 substituents]

| Comp. No. | R₁ | R₂ | R₃ | Phys. constant m.p. |
|---|---|---|---|---|
| 6.78 | H | H | CH₂—cyclopropyl | |
| 6.79 | H | H | CH₃ | |
| 6.80 | CH₃ | CH₃ | H | |
| 6.81 | C₂H₅ | CH₃ | H | |
| 6.82 | CH₃ | —C₆H₅ | H | |
| 6.83 | CH₃ | —CH₂—O—CH₃ | H | |
| 6.84 | CH₃ | —CH₂—O—CH₃ | CH₃ | |
| 6.85 | CH₃ | —C₆H₄—C₆H₅(p) | H | |
| 6.86 | CH₃ | —C₆H₅(4-Cl) | H | |
| 6.87 | CH₃ | 4-C₆H₄—OnC₃H₇ | CH₃ | 99–100° C. |
| 6.88 | CH₃ | 4-C₆H₄—OCH₂C₆H₄CF₃(3') | CH₃ | |
| 6.89 | CH₃ | 4-C₆H₄—OisoC₃H₇ | CH₃ | |
| 6.90 | CH₃ | 4-C₆H₄—OC₂H₅ | CH₃ | |
| 6.91 | CH₃ | —C₆H₃F₂(2,4) | CH₃ | Wax |
| 6.92 | CH₃ | 4-C₆H₄—OnC₄H₉ | CH₃ | |
| 6.93 | CH₃ | —C₆H₃(CH₃)₂(2,4) | CH₃ | |
| 6.94 | CH₃ | —C₆H₃(CH₃)₂(2,3) | CH₃ | |
| 6.95 | CH₃ | —C₆H₃(CH₃)₂(2,5) | CH₃ | |
| 6.96 | CH₃ | —C₆H₃CH₃(2),F(4) | CH₃ | |
| 6.97 | CH₃ | —C₆H₃CH₃(2),F(5) | CH₃ | |
| 6.98 | CH₃ | 4-C₆H₄—O—C₆H₄CF₃(3) | CH₃ | |
| 6.99 | CH₃ | 4-C₆H₄—O—C₆H₄Cl(4) | CH₃ | |
| 6.100 | CH₃ | 4-C₆H₄—O-Allyl | CH₃ | |
| 6.101 | CH₃ | 4-C₆H₄—OCF₃ | CH₃ | |
| 6.102 | CH₃ | 4-C₆H₄—OCH₂Si(CH₃)₃ | CH₃ | |
| 6.103 | CH₃ | 4-C₆H₄—OCH₃ | CH₃ | |
| 6.104 | CH₃ | 4-C₆H₄—Osec.C₄H₉ | CH₃ | |
| 6.105 | CH₃ | 4-C₆H₄—OisoC₄H₉ | CH₃ | |
| 6.106 | CH₃ | 4-C₆H₄—OCH=CCl₂ | CH₃ | |
| 6.107 | CH₃ | 4-C₆H₄—ON=C(CH₃)₂ | CH₃ | |
| 6.108 | CH₃ | 4-C₆H₄—O-Cyclopentyl | CH₃ | |
| 6.109 | CH₃ | —C₆H₃F(2)-OnC₃H₇(4) | CH₃ | |
| 6.110 | CH₃ | —C₆H₃F(2)-OC₂H₅(4) | CH₃ | |
| 6.111 | CH₃ | —C₆H₃F(2)-OisoC₃H₇(4) | CH₃ | |
| 6.112 | CH₃ | —C₆H₃F(2)-OCH₃(4) | CH₃ | |
| 6.113 | CH₃ | [3-fluoro-4-methylphenoxymethyl-(2,2-dichlorocyclopropyl)] | CH₃ | |
| 6.114 | CH₃ | —C₆H₃OCH₃(2)F(4) | CH₃ | |
| 6.115 | CH₃ | —C₆H₃OCH₃(2)CH₃(4) | CH₃ | |
| 6.116 | CH₃ | —C₆H₃CH₃(2)-OCH₃(4) | CH₃ | |
| 6.117 | CH₃ | —C₆H₃CH₃(2)-OC₂H₅(4) | CH₃ | |
| 6.118 | CH₃ | —C₆H₃CH₃(2)-OnC₃H₇(4) | CH₃ | |
| 6.119 | CH₃ | —C₆H₃CH₃(2)-OisoC₃H₇(4) | CH₃ | |
| 6.120 | CH₃ | —C₆H₄—OnC₃H₇(4) | CH₂CH₃ | |
| 6.121 | CH₃ | —C₆H₄—OC₂H₅(4) | CH₂CH₃ | |
| 6.122 | CH₃ | —C₆H₄—OnC₃H₇(4) | CH₂F | |
| 6.123 | CH₃ | —C₆H₄—OnC₃H₇(4) | CH₂—C≡CH | |
| 6.124 | CH₃ | —C₆H₄—OnC₃H₇(4) | (CH₂)₂CH₃ | |
| 6.125 | CH₃ | —C₆H₄—OnC₃H₇(4) | CH(CH₃)₂ | |
| 6.126 | CH₃ | —C₆H₄—OnC₃H₇(4) | CH₂—CH=CH₂ | |
| 6.127 | CH₃ | 2-Tolyl | CH₂CH₃ | |
| 6.128 | CH₃ | —C₆H₃F(2)CH₃(4) | CH₃ | |
| 6.129 | CH₃ | —C₆H₃F(2)CH₃(5) | CH₃ | |

TABLE 6-continued

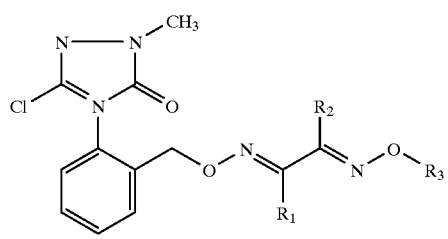

| Comp. No. | $R_1$ | $R_2$ | $R_3$ | Phys. constant m.p. |
|---|---|---|---|---|
| 6.130 | $CH_3$ | —$C_6H_3F_2$(2,5) | $CH_3$ | |
| 6.131 | $CH_3$ | —$C_6H_4$—$OCH_2CF_3$(4) | $CH_3$ | |
| 6.132 | $CH_3$ | —$C_6H_4C_2H_5$(4) | $CH_3$ | |
| 6.133 | $CH_3$ | —$COOCH_2CH=CH_2$ | $CH_3$ | |
| 6.134 | $CH_3$ | —$C_6H_4$—$OCHF_2$(4) | $CH_3$ | |
| 6.135 | $CH_3$ | 4-$C_6H_4$—O—$C_6H_4F$(4') | $CH_3$ | |
| 6.136 | $CH_3$ | —$COOCH(CH_3)_2$ | $CH_3$ | |
| 6.137 | $CH_3$ | —$C_6H_4Br$(4) | $CH_3$ | |
| 6.138 | $CH_3$ | 2-Pyridyl | $CH_3$ | |
| 6.139 | $CH_3$ | 3-Pyridyl | $CH_3$ | |
| 6.140 | $CH_3$ | 4-Pyridyl | $CH_3$ | |
| 6.141 | $CH_3$ | 2-Pyrazinyl | $CH_3$ | |
| 6.142 | $CH_3$ | 5,6-Dichloropyridinyl(3) | $CH_3$ | |
| 6.143 | $CH_3$ | $CH_3$ | $CF_2CHF_2$ | |
| 6.144 | $CH_3$ | 2-Fluoro-4-(4'-fluorobenzyloxy)-phenyl | $CH_3$ | |
| 6.145 | $CH_3$ | 4-$C_6H_4$—O—$C_6H_4Br$(3') | $CH_3$ | |
| 6.146 | $CH_3$ | —$C_6H_5$ | $CH_2C\equiv CH$ | |

TABLE 7

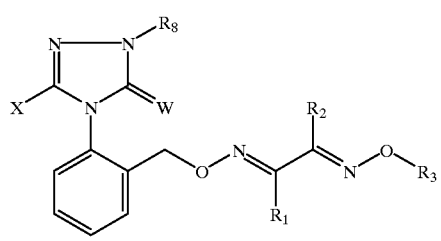

| Comp. No. | $R_1$ | $R_2$ | $R_3$ | $R_8$ | X | W | Phys. Dat. |
|---|---|---|---|---|---|---|---|
| 7.1 | $CH_3$ | $CH_3$ | $CH_3$ | $CH_3$ | $SCH_3$ | S | |
| 7.2 | $CH_3$ | $CH_3$ | $CH_3$ | $CF_3$ | $OCH_3$ | O | |
| 7.3 | $CH_3$ | $CH_3$ | $CH_3$ | Cyclopropyl | $OCH_3$ | O | |
| 7.4 | $CH_3$ | $CH_3$ | $CH_3$ | $CH_3$ | Cl | S | |
| 7.5 | $CH_3$ | $CH_3$ | $CH_3$ | $CH_3$ | $NHCH_3$ | O | |
| 7.6 | $CH_3$ | $CH_3$ | $CH_3$ | $CH_3$ | $N(CH_3)_2$ | O | |
| 7.7 | $CH_3$ | $CH_3$ | $CH_3$ | $CH_3$ | $NHCH_2CH=CH_2$ | O | |
| 7.8 | $CH_3$ | $CH_3$ | $CH_3$ | $CH_3$ | $NHCH_2C\equiv CH$ | O | |
| 7.9 | $CH_3$ | $CH_3$ | $CH_3$ | H | Cl | O | |
| 7.10 | Cyclopropyl | $CH_3$ | $CH_3$ | $CH_3$ | Cl | S | |
| 7.11 | $CH_3$ | —$C_6H_5$ | $CH_3$ | $CH_2CH_3$ | $SCH_3$ | O | |
| 7.12 | $CH_3$ | 4-$C_6H_4$—$C\equiv CH$ | $CH_3$ | $CH_2CH_3$ | $SCH_3$ | O | |
| 7.13 | $CH_3$ | $CH_3$ | $CH_2CH_3$ | $CH_3$ | Cl | S | |
| 7.14 | $CH_3$ | $CH_3$ | $CH_3$ | $CH_3$ | $SCH_2CH_3$ | O | |
| 7.15 | $CH_3$ | $CH_3$ | $CH_3$ | $CH_3$ | $OCH_2F$ | O | |
| 7.16 | $CH_3$ | 4-$C_6H_4$—$OCH_3$ | $CH_3$ | $CH_3$ | $SCH_3$ | S | |
| 7.17 | $CH_3$ | 4-$C_6H_4$—$OC_2H_5$ | $CH_2CH_3$ | $CH_3$ | Cl | O | |
| 7.18 | $CH_3$ | 2-Pyridyl | $CH_3$ | $CH_3$ | Cl | S | |
| 7.19 | $CH_3$ | —CN | $CH_2CF_3$ | $CH_3$ | $OCH_3$ | O | |
| 7.20 | Cyclopropyl | 2-Tolyl | $CH_3$ | $CH_3$ | $SCH_3$ | O | |
| 7.21 | $CH_3$ | $CH_2OCH_3$ | $CH_3$ | $CH_3$ | $SCH_3$ | S | |
| 7.22 | $CH_3$ | Cyclopropyl | $CH_2CH_3$ | $CH_3$ | Cl | O | |
| 7.23 | $CH_3$ | $COOi$-Propyl | $CH_3$ | $CH_3$ | Cl | O | |

TABLE 7-continued

| Comp. No. | R₁ | R₂ | R₃ | R₈ | X | W | Phys. Dat. |
|---|---|---|---|---|---|---|---|
| 7.24 | $CH_3$ | $CH_3$ | $CH_2$-(1,1-dichlorocyclopropyl) | $CH_3$ | $SCH_3$ | O | |
| 7.25 | $CH_3$ | $CH_3$ | $CH_2F$ | $CH_3$ | $SCH_3$ | S | |
| 7.26 | $CH_3$ | $CH_3$ | $CH_2CN$ | $CH_3$ | $OCH_3$ | O | |
| 7.27 | $CH_2CH_3$ | $CH_3$ | $CH_2CH_3$ | $CH_3$ | $OCH_3$ | O | |
| 7.28 | $CH_2CH_3$ | $CH_3$ | H | $CH_3$ | $OCH_3$ | S | |
| 7.29 | $CH_2CH_2CH_3$ | $CH_3$ | $CH_3$ | $CH_3$ | $SCH_3$ | O | |
| 7.30 | $CH_3$ | $CH_2CH_2CH_3$ | $CH_2CH_3$ | $CH_3$ | $OCH_3$ | O | |
| 7.31 | $CH_3$ | Cyclohexyl | $CH_3$ | $CH_3$ | $OCH_3$ | O | |
| 7.32 | $CH_3$ | S—$C_6H_4Cl(4)$ | $CH_3$ | $CH_3$ | $OCH_3$ | O | |
| 7.33 | $CH_3$ | O—$C_6H_4CF_3(3)$ | $CH_3$ | $CH_2CH_3$ | $OCH_3$ | O | |
| 7.34 | $CH_3$ | O-2-Pyridyl | $CH_2CH_3$ | $CH_3$ | $OCH_3$ | O | |
| 7.35 | $CH_3$ | 2-(4,5-dihydrothiazolyl) | $CH_3$ | $CH_3$ | $SCH_3$ | S | |
| 7.36 | $CH_3$ | 4-Methoxybenzyl | $CH_3$ | $CH_3$ | Cl | S | |
| 7.37 | $CH_3$ | $CH_2$-3-Pyridyl | $CH_3$ | $CH_3$ | $SCH_3$ | S | |
| 7.38 | $CH_3$ | —$C_6H_3F_2(2,4)$ | $CH_2CH_3$ | $CH_3$ | $OCH_3$ | O | |
| 7.39 | $CH_3$ | 4-Cyclopentoxyphenyl | $CH_2CH_2CH_3$ | $CH_3$ | $OCH_3$ | O | |
| 7.40 | $CH_3$ | 4-n-Propoxyphenyl | $CH_2CH_3$ | $CH_3$ | $SCH_3$ | S | |
| 7.41 | $CH_3$ | 4-sec.-Butoxyphenyl | $CH(CH_3)_2$ | $CH_3$ | $OCH_3$ | O | |
| 7.42 | $CH_3$ | 4-$C_6H_3F(2)OC_2H_5(4)$ | $CH_2CH_2F$ | $CH_3$ | $OCH_3$ | O | |
| 7.43 | $CH_3$ | 2,4-Xylyl | $CH_2CH=CH_2$ | $CH_3$ | $OCH_3$ | O | |
| 7.44 | $CH_3$ | 2,3-Xylyl | $CH_2C\equiv CH$ | $CH_3$ | $SCH_3$ | O | |
| 7.45 | $CH_3$ | $CH_2CH_3$ | $CH_2CH_2CH_3$ | $CH_3$ | $OCH_3$ | O | |
| 7.46 | $CH_3$ | 4-$C_6H_4$—O—$C_6H_4Cl(4')$ | $CH_2CH_3$ | $CH_3$ | $OCH_3$ | O | |
| 7.47 | $CH_3$ | 2-Fluoro-3-pyridyl | $CH_3$ | $CH_3$ | $OCH_3$ | O | |
| 7.48 | $CH_3$ | $CH_3$ | $CH_2OCH_3$ | $CH_3$ | Cl | S | |
| 7.49 | $CH_3$ | —$C_6H_5$ | H | $CH_3$ | Cl | S | |
| 7.50 | $CH_3$ | 4-$C_6H_4$—$OCH_2$-(2,2-dichlorocyclopropyl) | $CH_2CH_3$ | $CH_3$ | $OCH_3$ | O | |

TABLE 8

[Structure: 1,2,4-triazole with R8 on N, X on C, =W on C; N4 attached to phenyl bearing ortho-CH2-O-N=C(CH3)-C(R2)=N-OCH3]

| Comp. No. | R$_2$ | X | R$_8$ | W | Phys. Data |
|---|---|---|---|---|---|
| 8.1 | CH$_3$ | CH$_3$NH— | H | O | |
| 8.2 | CH$_3$ | CH$_3$NH— | C$_2$H$_5$ | O | |
| 8.3 | CH$_3$ | CH$_3$NH— | CF$_3$ | O | |
| 8.4 | CH$_3$ | CH$_3$NH— | Cyclopropyl | O | |
| 8.5 | CH$_3$ | CH$_3$NH— | CH$_3$ | S | |
| 8.6 | CH$_3$ | (CH$_3$)$_2$N— | CH$_3$ | O | |
| 8.7 | CH$_3$ | (CH$_3$)$_2$N— | H | O | |
| 8.8 | CH$_3$ | (CH$_3$)$_2$N— | CF$_3$ | O | |
| 8.9 | CH$_3$ | (CH$_3$)$_2$N— | Cyclopropyl | O | |
| 8.10 | CH$_3$ | (Allyl)N(CH$_3$)— | CH$_3$ | O | |
| 8.11 | CH$_3$ | (Allyl)N(CH$_3$)— | H | O | |
| 8.12 | CH$_3$ | (Allyl)N(CH$_3$)— | CF$_3$ | O | |
| 8.13 | CH$_3$ | (Allyl)N(CH$_3$)— | Cyclopropyl | O | |
| 8.14 | CH$_3$ | (Allyl)N(CH$_3$)— | CH$_3$ | S | |
| 8.15 | CH$_3$ | (Propargyl)N(CH$_3$)— | CH$_3$ | O | |
| 8.16 | CH$_3$ | (Propargyl)N(CH$_3$)— | H | O | |
| 8.17 | CH$_3$ | (Propargyl)N(CH$_3$)— | C$_2$H$_5$ | O | |
| 8.18 | CH$_3$ | (Propargyl)N(CH$_3$)— | CF$_3$ | O | |
| 8.19 | CH$_3$ | (Propargyl)N(CH$_3$)— | Cyclopropyl | O | |
| 8.20 | CH$_3$ | (Propargyl)$_2$N— | CH$_3$ | O | |
| 8.21 | CH$_3$ | (Propargyl)$_2$N— | H | O | |
| 8.22 | CH$_3$ | (Propargyl)$_2$N— | isoC$_3$H$_7$ | O | |
| 8.23 | CH$_3$ | (Propargyl)$_2$N— | CF$_3$ | O | |
| 8.24 | CH$_3$ | (Propargyl)$_2$N— | Cyclopropyl | O | |
| 8.25 | CH$_3$ | (Propargyl)$_2$N— | CH$_3$ | S | |
| 8.26 | 2-Tolyl | Cl | CH$_3$ | O | |
| 8.27 | CH$_3$ | Cl | C$_2$H$_5$ | O | |
| 8.28 | CH$_3$ | Cl | CH$_3$ | S | |
| 8.29 | CH$_3$ | Cl | CF$_3$ | O | |
| 8.30 | CH$_3$ | Cl | Cyclopropyl | O | |
| 8.31 | 4-Tolyl | CH$_3$S— | CH$_3$ | O | |
| 8.32 | CH$_3$ | CH$_3$S— | H | O | |
| 8.33 | CH$_3$ | CH$_3$S— | C$_2$H$_5$ | O | |
| 8.34 | CH$_3$ | CH$_3$S— | CF$_3$ | O | |
| 8.35 | CH$_3$ | CH$_3$S— | Cyclopropyl | O | |
| 8.36 | CH$_3$ | CH$_3$S— | Cyclopentyl | O | |
| 8.37 | CH$_3$ | CF$_3$O— | CH$_3$ | O | |
| 8.38 | CH$_3$ | CF$_3$O— | H | O | |
| 8.39 | CH$_3$ | CF$_3$O— | CH$_3$ | S | |
| 8.40 | 2-C$_6$H$_4$—C≡CH | CH$_3$O— | CH$_3$ | O | |
| 8.41 | 3-C$_6$H$_4$—C≡CH | CH$_3$O— | CH$_3$ | O | |
| 8.42 | 3-C$_6$H$_4$—C≡C—CH$_3$ | CH$_3$O— | CH$_3$ | O | |
| 8.43 | 4-C$_6$H$_4$—C≡C—CH$_3$ | CH$_3$O— | CH$_3$ | O | |
| 8.44 | 2-C$_6$H$_4$—C≡C—C$_2$H$_5$ | CH$_3$O— | CH$_3$ | O | |
| 8.45 | 4-C$_6$H$_4$—C≡C—C$_6$H$_5$ | CH$_3$O— | CH$_3$ | O | |
| 8.46 | 4-C$_6$H$_4$—C≡C—Br | CH$_3$O— | CH$_3$ | O | |
| 8.47 | 4-C$_6$H$_4$—C≡C—J | CH$_3$O— | CH$_3$ | O | |
| 8.48 | 4-C$_6$H$_4$—C≡C—CN | CH$_3$O— | CH$_3$ | O | |
| 8.49 | 4-C$_6$H$_4$—C≡C—C(CH$_3$)$_2$OH | CH$_3$O— | CH$_3$ | O | |
| 8.50 | 3-C$_6$H$_4$—C≡C—C(CH$_3$)$_2$OH | CH$_3$O— | CH$_3$ | O | |
| 8.51 | 2-C$_6$H$_4$—C≡C—C(CH$_3$)$_2$OH | CH$_3$O— | CH$_3$ | O | |
| 8.52 | 4-C$_6$H$_4$—C≡C—COOCH$_3$ | CH$_3$O— | CH$_3$ | O | |
| 8.53 | 4-C$_6$H$_4$—C≡C—CH(CH$_3$)=CH$_2$Cl | CH$_3$O— | CH$_3$ | O | |
| 8.54 | 4-C$_6$H$_4$—C≡C—CO—N(CH$_3$)OCH$_3$ | CH$_3$O— | CH$_3$ | O | |
| 8.55 | 4-C$_6$H$_4$—C≡C-Pyridyl(3) | CH$_3$O— | CH$_3$ | O | |
| 8.56 | 4-C$_6$H$_4$—C≡C-Pyrimidinyl(5) | CH$_3$O— | CH$_3$ | O | |
| 8.57 | 4-C$_6$H$_4$—C≡C-Pyrazinyl(2) | CH$_3$O— | CH$_3$ | O | |
| 8.58 | 4-C$_6$H$_4$—C≡C—C(CH$_3$)$_2$—OH | Cl | CH$_3$ | O | |
| 8.59 | 4-C$_6$H$_4$—C≡CH | Cl | CH$_3$ | O | |
| 8.60 | 4-C$_6$H$_4$—C≡CBr | Cl | CH$_3$ | O | |
| 8.61 | 4-C$_6$H$_4$—C≡C-Pyrazinyl(2) | Cl | CH$_3$ | O | |
| 8.62 | 4-C$_6$H$_4$—C≡C-Pyridyl(3) | Cl | CH$_3$ | O | |
| 8.63 | 4-C$_6$H$_4$—C≡C—CN | Cl | CH$_3$ | O | |

TABLE 8-continued

| Comp. No. | R₂ | X | R₈ | W | Phys. Data |
|---|---|---|---|---|---|
| 8.64 | 4-C₆H₄—C≡C—COOC₂H₅ | Cl | CH₃ | O | |
| 8.65 | 4-C₆H₄—C≡C-Pyridyl(3) | CH₃S | CH₃ | O | |
| 8.66 | 4-C₆H₄—C≡C-Pyridyl(2) | Cl | CH₃ | O | |
| 8.67 | 4-C₆H₄—C≡C-Pyridyl(4) | Cl | CH₃ | O | |
| 8.68 | 4-C₆H₄—C≡C-Pyridyl(3) | CH₃NH— | CH₃ | O | |
| 8.69 | —COOCH₂—cyclopropyl | CH₃NH— | CH₃ | O | |
| 8.70 | 4-C₆H₄—C≡CH | CF₃O— | CH₃ | O | |
| 8.71 | 4-C₆H₄—C≡CH | (Propargyl)₂N— | CH₃ | O | |
| 8.72 | 4-C₆H₄—C≡CH | (Allyl)₂N— | CH₃ | O | |
| 8.73 | 4-C₆H₄—C≡CH | (CH₃)₂N— | CH₃ | O | |
| 8.74 | 3-C₆H₄—C≡CH | CH₃NH— | CH₃ | O | |
| 8.75 | 3-C₆H₄—C≡CH | CH₃NH— | CH₃ | S | |
| 8.76 | 2-C₆H₄—C≡CH | CH₃NH— | CH₃ | O | |
| 8.77 | 2-C₆H₄—C≡CH | (CH₃)₂N— | CH₃ | O | |
| 8.78 | 2-C₆H₄—C≡CH—C(CH₃)₂—OH | Cl | CH₃ | O | |
| 8.79 | 3-C₆H₄—C≡C—C(CH₃)₂—OH | Cl | CH₃ | O | |
| 8.80 | 4-C₆H₄—C≡C—C₆H₄OH(4) | CH₃O | CH₃ | O | |

TABLE 9

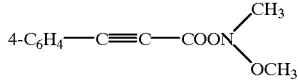

| Comp. No. | R₁ | R₂ | R₃ | Phys. Data m.p. |
|---|---|---|---|---|
| 9.1 | CH₃ | 2-C₆H₄—C≡CH | CH₃ | Oil |
| 9.2 | CH₃ | 3-C₆H₄—C≡CH | CH₃ | |
| 9.3 | CH₃ | 4-C₆H₄—C≡CH | CH₃ | |
| 9.4 | CH₃ | 2-C₆H₄—C≡C—C(CH₃)₂OH | CH₃ | |
| 9.5 | CH₃ | 3-C₆H₄—C≡C—C(CH₃)₂OH | CH₃ | |
| 9.6 | CH₃ | 4-C₆H₄—C≡C—C(CH₃)₂OH | CH₃ | |
| 9.7 | CH₃ | 2-C₆H₄—C≡C—CH₃ | CH₃ | |
| 9.8 | CH₃ | 3-C₆H₄—C≡C—CH₃ | CH₃ | |
| 9.9 | CH₃ | 4-C₆H₄—C≡C—C₂H₅ | CH₃ | |
| 9.10 | CH₃ | 4-C₆H₄—C≡C—Br | CH₃ | |
| 9.11 | CH₃ | 4-C₆H₄—C≡C—CN | CH₃ | |
| 9.12 | CH₃ | 4-C₆H₄—C≡C—COOC₂H₅ | CH₃ | |
| 9.13 | CH₃ | 4-C₆H₄—C≡C-Pyridyl(3) | CH₃ | |
| 9.14 | CH₃ | 4-C₆H₄—C≡C-Pyridyl(4) | C₂H₅ | |
| 9.15 | CH₃ | 4-C₆H₄—C≡C-Pyrazinyl(2) | CH₃ | |
| 9.16 | Cyclopropyl | 4-C₆H₄—C≡C-Thienyl(3) | CH₃ | |
| 9.17 | Cyclopropyl | 4-C₆H₄—C≡C—COON(CH₃)(OCH₃) | Allyl | |

TABLE 9-continued

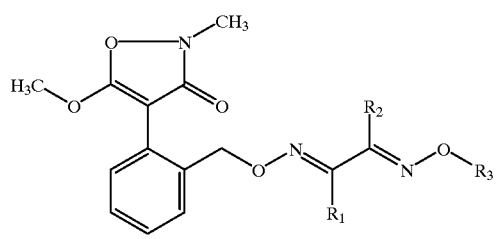

| Comp. No. | R₁ | R₂ | R₃ | Phys. Data m.p. |
|---|---|---|---|---|
| 9.18 | CH₃ | 4-C₆H₄—C≡C—CF₃ | CH₃ | |
| 9.19 | CH₃ | 3-C₆H₄—C≡C—CF₃ | CH₃ | |
| 9.20 | CH₃ | 4-C₆H₄—C≡C—COOCH₂Cyclopropyl-(Cl)₂(2',2') | Ethyl | |
| 9.21 | CH₃ | 2-C₆H₄—C≡C—CH(CH₃)=CH₂ | CH₃ | |
| 9.22 | CH₃ | 3-C₆H₄—C≡C—CH(CH₃)=CH₂ | CH₃ | |
| 9.23 | CH₃ | 4-C₆H₄—C≡C—CH(CH₃)=CH | CH₃ | |
| 9.24 | CH₃ | 4-C₆H₄—C≡C—C₆H₅ | CH₃ | |
| 9.25 | CH₃ | 4-C₆H₄—C≡C—C₆H₃Cl₂(2,4) | CH₃ | |
| 9.26 | CH₃ | 4-C₆H₄—C≡C—C₆H₃CH₃(2)Cl(4) | CH₃ | |
| 9.27 | CH₃ | 4-C₆H₄—C≡C—C₆H₄OH(4) | CH₃ | |
| 9.28 | CH₃ | 4-C₆H₄—C≡C—C₆H₄OH(3) | CH₃ | |

2. Formulation Examples for active ingredients of formula I (% = percent by weight)

2.1. Wettable powder

| | a) | b) | c) |
|---|---|---|---|
| Active ingredient from Tables 1–9 | 25% | 50% | 75% |
| Na ligninsulfonate | 5% | 5% | — |
| Na lauryl sulfate | 3% | — | 5% |
| Na diisobutylnaphthalenesulfonate | — | 6% | 10% |
| Octylphenol polyethylene glycol ether (7–8 mol of ethylene oxide) | — | 2% | — |
| Highly disperse silicic acid | 5% | 10% | 10% |
| Kaolin | 62% | 27% | — |

The active ingredient is mixed thoroughly with the additives and the mixture is ground thoroughly in an appropriate mill. This gives wettable powders which can be diluted with water to give suspensions of any desired concentration.

2.2. Emulsion concentrate

| | |
|---|---|
| Active ingredient of Tables 1–9 | 10% |
| Octylphenol polyethylene glycol ether (4 . 5 mol of ethylene oxide) | 3% |
| Ca dodecylbenzenesulfonate | 3% |
| Cyclohexanone | 34% |
| Xylene mixture | 50% |

Emulsions of any desired dilution can be prepared from this concentrate by dilution with water.

2.3. Dust

| | a) | b) |
|---|---|---|
| Active ingredient from Tables 1–9 | 5% | 8% |
| Talc | 95% | — |
| Kaolin | — | 92% |

Ready-to-use dusts are obtained by mixing the active ingredient with the carrier and grinding the mixture on an appropriate mill.

2.4. Extruded granules

| | |
|---|---|
| Active ingredient from Tables 1–9 | 10% |
| Na ligninsulfonate | 2% |
| Carboxymethylcellulose | 1% |
| Kaolin | 87% |

The active ingredient is mixed with the additives and the mixture is ground and moistened with water. This mixture is extruded and then dried in a stream of air.

2.5. Coated granules

| | |
|---|---|
| Active ingredient from Tables 1–9 | 3% |
| Polyethylene glycol (MW 200) | 3% |
| Kaolin | 94% |

(MW = molecular weight)

The finely ground active ingredient is coated uniformly in a mixer onto the kaolin, which has been moistened with polyethylene glycol. In this way, dust-free coated granules are obtained.

2.6. Suspension concentrate

| | |
|---|---|
| Active ingredient from Tables 1–9 | 40% |
| Ethylene glycol | 10% |
| Nonylphenol polyethylene glycol ether (15 mol of ethylene oxide) | 6% |
| Na ligninsulfonate | 10% |
| Carboxymethylcellulose | 1% |
| 37% aqueous formaldehyde solution | 0.2% |
| Silicone oil in the form of 75% aqueous emulsion | 0.8% |
| Water | 32% |

The finely ground active ingredient is intimately mixed with the additives to give a suspension concentrate from which suspensions of any desired dilution can be prepared by diluting with water.

3. BIOLOGICAL EXAMPLES

Example B-1
Action Against Phytophthora Infestans on Tomatoes a) Curative action Tomato plants cv. "Roter Gnom" are grown for three weeks and then sprayed with a zoospore suspension of the fungus and incubated in a cabinet at 18 to 20° and saturated atmospheric humidity. Humidification is interrupted after 24 hours. After the plants have dried, they are sprayed with a mixture which comprises the active ingredient, formulated as a wettable powder, at a concentration of 200 ppm. After the spray coating has dried on, the plants are returned to the humid cabinet for 4 days. The number and size of the typical leaf spots which have developed after this period are used to assess the activity of the test substances.

b) Preventive-systemic action

The active ingredient formulated as a wettable powder, is applied in a concentration of 60 ppm (relative to the volume of soil) to the soil surface of three-week-old tomato plants cv. "Roter Gnom" in pots. After waiting for three days, the underside of the leaves is sprayed with a zoospore suspension of Phytophthora infestans. The plants are then kept for 5 days in a spray cabinet at 18 to 20° C. and saturated atmospheric humidity. After this period, typical leaf spots develop, whose number and size are used to assess the activity of the test substances.

While untreated but infected control plants show an infestation of 100%, the active ingredients of the formula I in accordance with one of Tables 1 to 9 suppress infestation in one of the two tests to 10% or less. A particularly good action is shown by Comp. 3.87.

Example B-2
Action Against *Plasmopara viticola* (Bert. et Curt.) (Berl. et DeToni) on Vines a) Residual-preventive action Vine cuttings cv. "Chasselas" are grown in a greenhouse. When they have reached the 10-leaf stage, 3 plants are sprayed with a mixture (200 ppm of active ingredient). After the spray coating has dried on, the leaf underside is infected uniformly with a spore suspension of the fungus. The plants are subsequently kept in a humid cabinet for 8 days. After this period, marked disease symptoms are evident on the control plants. The number and size of the infection sites on the treated plants are used to assess the activity of the test substances.

b) Curative action

Vine cuttings cv. "Chasselas" are grown in a greenhouse and, on reaching the 10-leaf stage, are infected on the underside of the leaves with a spore suspension of *Plasmopara viticola*. After the plants have remained for 24 hours in a humid cabinet, they are sprayed with a mixture of active ingredient (200 ppm of active ingredient). The plants are subsequently kept for 7 days more in the humid cabinet. After this period, the disease symptoms are evident on the control plants. The number and size of the infection sites on the treated plants are used to assess the activity of the test substances.

In comparison with the control plants, the infestation of plants which have been treated with active ingredients of the formula I is 20% or less. A particularly good action is shown by Comp. 3.87.

Example B-3
Action Against *Pythium debaryanum* on Sugar Beet (*Beta vulgaris*)

a) Action after soil application

The fungus is grown on sterile oat grains and added to a mixture of soil and sand. The soil infected in this way is placed in flower pots and sown with sugar beet seeds. Immediately after sowing, the test preparations, formulated as wettable powders, are poured over the soil in the form of an aqueous suspension (20 ppm of active ingredient relative to the volume of soil). The pots are then placed in a greenhouse for 2–3 weeks at 20–24° C. All the time, the soil is kept uniformly moist by spraying it gently with water. When the tests are evaluated, the emergence of the sugar beet plants and the proportion of healthy and diseased plants is determined.

b) Action after seed dressing

The fungus is grown on sterile oat grains and added to a mixture of soil and sand. The soil infected in this way is placed in flower pots and sown with sugar beet seeds which have been dressed with the test preparations, formulated as seed-dressing powders (1000 ppm of active ingredient relative to the weight of seed). The pots in which beet has been sown are placed in a greenhouse at 20–24° C. for 2–3 weeks. During this time, the soil is kept uniformly moist by spraying it gently with water.

When the test is evaluated, the emergence of the sugar beet plants and the proportion of healthy and diseased plants is determined.

After the treatment with active ingredients of the formula I, over 80% of the plants emerge and have a healthy appearance. In the control pots, only a few plants of unhealthy appearance have emerged.

Example B-4
Residual-Protective Action Against *Cercospora arachidicola* on Ground Nuts 10 to 15 cm high ground nut plants are sprayed to drip point with an aqueous spray mixture (0.02% of active substance) and, 48 hours later, are infected with a conidia suspension of the fungus. The plants are incubated for 72 hours at 21° and high atmospheric humidity and subsequently placed in a greenhouse until typical leaf spots have appeared. The action of the active substance is evaluated 12 days after the infection on the basis of the number and size of the leaf spots.

Active ingredients of the formula I bring about a reduction in leaf spots to less than approximately 10% of the leaf surface area. In some cases, the disease is suppressed completely (0–5% infestation).

Example B-5
Action Against *Puccinia graminis* on Wheat a) Residual-protective action 6 days after sowing, wheat plants are sprayed to drip point with an aqueous spray mixture (0.02% of active substance) and, 24 hours later, are infected with a uredospore suspension of the fungus. After an incubation period of 48 hours (conditions: 95 to 100 per cent relative atmospheric humidity at 20°) the plants are placed in a greenhouse at 22°. The development of rust pustules is assessed 12 days after infection.

b) Systemic action 5 days after sowing, an aqueous spray mixture (0.006% of active substance, relative to the volume of soil) is poured next to wheat plants. Contact of the spray mixture with aerial parts of the plants is carefully avoided. 48 hours later, the plants are infected with a uredospore suspension of the fungus. After an incubation period of 48 hours (conditions: 95 to 100 per cent relative atmospheric humidity at 20°) the plants are placed in a greenhouse at 22°. The development of rust pustules is assessed 12 days after infection Compounds of the formula I bring about a marked reduction in fungal infestation, in some cases down to 10–0%, for example Compounds 1.1; 3.1; 3.7; 3.13; 3.16; 3.19; 7.2; 7.12; 7.5; 7.7; 7.43; 8.10; 8.27; 8.40; 8.43; 8.55; 8.57; 8.61; 8.62; 9.1; 9.13 and others.

Example B-6
Action Against *Pyricularia oryzae* on Rice
  a) Residual-protective action
  Rice plants are grown for two weeks and sprayed to drip point with an aqueous spray mixture (0.02% of active substance), and, 48 hours later, are infected with a conidia suspension of the fungus. Fungal infestation is assessed 5 days after infection, during which period the relative atmospheric humidity is kept at 95 to 100 per cent and the temperature at 22 °.
  b) Systemic action
  An aqueous spray mixture (0.006% of active substance, relative to the volume of soil) is poured next to 2-week-old rice plants. Contact of the spray mixture with the aerial parts of the plants is carefully avoided. The pots are then filled with water such that the lowest parts of the stems of the rice plants are submerged. After 96 hours, the plants are infected with a conidia suspension of the fungus and are kept for 5 days at a relative atmospheric humidity of 95 to 100 per cent and at a temperature of 24° C.
  In most cases, compounds of the formula I prevent the outbreak of disease on the infected plants.

Example B-7
Residual-Protective Action Against *Venturia inaegualis* on Apples
  Apple cuttings having fresh shoots 10 to 20 cm in length are sprayed to drip point with a spray mixture (0.02% of active substance) and, 24 hours later, are infected with a conidia suspension of the fungus. The plants are incubated for 5 days at a relative atmospheric humidity of 90 to 100 per cent and then placed for 10 days more in a greenhouse at 20 to 24°. Infestation with scab is assessed 15 days after infection.
  The majority of compounds of the formula I from one of Tables 1 to 9 have a sustained action against scab diseases.

Example B-8
Action Against *Erysiphe graminis* on Barley
  a) Residual-protective action
  Barley plants about 8 cm in height are sprayed to drip point with an aqueous spray mixture (0.02% of active substance) and, 3 to 4 hours later, are dusted with conidia of the fungus. The infected plants are placed in a greenhouse at 22°. Fungal infestation is assessed 10 days after infection.
  b) Systemic action
  An aqueous spray mixture (0.002% of active substance, relative to the volume of soil) is poured next to barley plants which are approximately 8 cm high. Contact of the spray mixture with aerial parts of the plant is carefully avoided. 48 hours later, the plants are dusted with conidia of the fungus. The infected plants are placed in a greenhouse at 22°. Fungal infestation is assessed 10 days after infection.
  Compounds of the formula I are generally capable of reducing the level of disease to less than 20%, and in some cases completely, examples being Compounds 1.1; 3.1; 3.7; 3.13; 3.16; 3.19; 7.2; 7.12; 7.5; 7.7; 7.43; 8.10; 8.27; 8.40; 8.43; 8.55; 8.57; 8.61; 8.62; 9.1; 9.13 and others.

Example B-9
Action Against *Podosphaera leucotricha* on Apple Shoots
  Residual-protective action
  Apple cuttings having fresh shoots about 15 cm long are sprayed with a spray mixture (0.06% of active substance). After 24 hours, the treated plants are infected with a conidia suspension of the fungus and are placed in a controlled-environment cabinet at a relative atmospheric humidity of 70% and at 20° C. Fungal infestation is assessed 12 days after infection.
  Active ingredients of the formula I suppress the level of disease to less than 20%. Control plants show a disease level of 100%.

Example B-10
Action Against *Botrytis cinerea* on Apple Fruits Residual-Protective Action
  Artifically wounded apples are treated by applying dropwise a spray mixture (0.02% of active substance) to the wounds. The treated fruits are subsequently inoculated with a spore suspension of the fungus and are incubated at high atmospheric humidity and about 20° C. for one week. The fungicidal action of the test substance is derived from the number of wounds showing signs of rot.
  Active ingredients of the formula I from Tables 1 to 9 are able to prevent the spread of the rot, in some cases completely.

Example B-11
Action Against *Helminthosporium gramineum*
  Wheat grains are contaminated with a spore suspension of the fungus and allowed to dry. The contaminated grains are dressed with a suspension of the test substance (600 ppm of active ingredient, relative to the weight of the seeds). After two days, the grains are arranged in suitable dishes containing agar, and after four days more the development of fungal colonies around the grains is assessed. The number and size of the fungal colonies are used to evaluate the test substance.
  Compounds of the formula I show in some cases a good action, i.e. inhibition, of the fungal colonies.

Example B-12
Action Against *Colletotrichum lagenarium* on Cucumbers
  Cucumber plants are grown for 2 weeks and then sprayed with a spray mixture (concentration 0.002%). After 2 days, the plants are infected with a spore suspension ($1.5 \times 10^5$ spores/ml) of the fungus and are incubated for 36 hours at 23° C. at a high atmospheric humidity. Incubation is then continued at normal atmospheric humidity and at about 22–23° C. The fungal infestation which has developed is assessed 8 days after infection. Untreated but infected control plants show fungal infestation of 100%. Compounds of the formula I cause in some cases almost complete inhibition of the disease.

Example B-13
Action Against *Fusarium nivale* on Rye
  Rye cv. Tetrahell naturally infected with *Fusarium nivale* is dressed with the test fungicide using a mixing roller, the following concentrations being employed: 20 or 6 ppm of a.i. (relative to the weight of seed).
  Using a seed drill, the infected and treated rye is drilled in October in a field in 3 m plots with 6 seed furrows, with 3 replicates per concentration.
  Until infestation is evaluated, the test plants are grown under normal field conditions (preferably in a region with a complete covering of snow during the winter months).
  To assess the phytotoxicity, seed emergence is rated in autumn, and the number of plants per unit area/number of tillers per plant in spring.
  To determine the activity of the active ingredient, the percentage of Fusarium-infested plants is counted immediately after the snow has melted in the early part of the year. The number of infected plants was less than 5% in the case of treatment with a compound of the formula I. The plants which emerged were of healthy appearance.

Example B-14
Action Against *Septoria nodorum* on Wheat
  Wheat plants in the 3-leaf stage was sprayed with a spray mixture (60 ppm of a.i.) prepared from a wettable powder of the active substances.
  After 24 hours, the treated plants are infected with a conidia suspension of the fungus. The plants are then incubated for 2 days at 90–100% relative atmospheric humidity and placed in a greenhouse at 20–24° C. for 10 days more. 13 days after infection, fungal infestation is assessed. Less than 1% of the wheat plants showed disease.

Example B-15

Action Against *Rhizoctonia solani* on Rice

Protective-local soil application:

10-day-old rice plants in a flowerpot were watered with a suspension (spray mixture) prepared with a formulated test substance, without aerial parts of the plants being contaminated with the suspension. 3 days later, the plants are infected by placing a stem of barley straw infected with *Rhizoctonia solani* between the rice plants of each pot. After incubation for 6 days in a controlled-environment room at a daytime temperature of 29° C. and a nighttime temperature of 26° C. and 95% relative atmospheric humidity, fungal infestation is assessed. Less than 5% of the rice plants are infected. The plants had a healthy appearance.

Protective-local foliar application 12-day-old rice plants are sprayed with a suspension prepared from formulated test substances. One day later, the plants are infected by placing a stem of barley straw infected with *Rhizoctonia solani* between the rice plants of each pot. After incubation for 6 days in a controlled-environment room at a day time temperature of 9° C. and a night time temperature of 26° C. and 95% relative atmospheric humidity, the test is rated. Untreated but infected control plants show fungal infestation of 100%. Compounds of the formula I bring about in some cases complete inhibition of the disease.

Insecticial Action

Example B-16

Action Against *Heliothis virescens*

Young soya bean plants are sprayed with an aqueous emulsion spray mixture comprising 100 ppm of active ingredient; then, after the spray coating has dried on, the plants are populated with 10 first-stage caterpillars of *Heliothis virescens* and subsequently placed in a plastic container. By comparing the number of dead caterpillars and the feeding damage of the treated and untreated plants, 6 days later, the percentage reduction in population and the feeding damage (% action) are determined.

Compounds of the formula I show a good action in this test (mortality rate>90%).

Example B-17

Action Against *Spodoptera littoralis*

Young soya bean plants are sprayed with an aqueous emulsion spray mixture comprising 100 ppm of active substance; then, after the spray coating is dried on, the plants are populated with 10 third-stage caterpillars of *Spodoptera littoralis* and are subsequently placed in a plastic container. By comparing the number of dead caterpillars and the feeding damage between the treated and untreated plants, three days later, the percentage reduction in the population and the percentage reduction in feeding damage (% action) are determined.

Compounds from Tables 1–9 show good action in this test.

Example B-22

Action Against *Plutella xylostella* Caterpillars

Young cabbage plants are sprayed with an aqueous emulsion spray mixture comprising 100 ppm of active ingredient. After the spray coating has dried on, the cabbage plants are populated with 10 third-stage caterpillars of *Plutella xylostella* and are placed in a plastic container. Evaluation is made 3 days later. By comparing the number of dead caterpillars and the feeding damage on the treated plants to that on the untreated plants, the percentage reduction in population and, respectively, the percentage reduction in feeding damage (% action) are determined.

Compounds from the tables show good action.

What is claimed is:

1. A bis-oxime derivative of the formula I

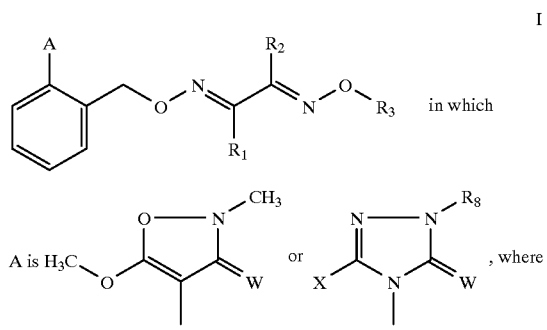

in which

W is oxygen or sulfur, and the other are substituents defined as follows:

$R_1$=hydrogen, $C_1$–$C_4$alkyl; cyclopropyl;

$R_2$=hydrogen, $C_1$–$C_6$alkyl; halo($C_1$–$C_6$)alkyl; $C_2$–$C_6$alkoxyalkyl; $C_3$–$C_6$cycloalkyl; substituded or unsubstituted aryl; substituted or unsubstituted heteroaryl; cyano; $C_1$–$C_6$alkoxycarbonyl; $C_1$–$C_6$alkyl-S(O)$_n$; substituted or unsubstituted aryl-S(O)$_n$; $C_1$–$C_6$alkoxy; substituted or unsubstituted aryloxy; substituted or unsubstituted heteroaryloxy; unsubstituted or mono- to trimethyl-substituted heterocyclyl; substituted or unsubstituted aryl-$C_1$–$C_6$alkyl; substituted or unsubstituted heteroaryl-$C_1$–$C_6$alkyl;

$R_3$=hydrogen; $C_1$–$C_6$alkyl; $C_1$–$C_6$haloalkyl having 1 to 5 halogen atoms; $C_1$–$C_4$alkoxy-$C_1$–$C_2$alkyl; unsubstituted or mono- to trihalo-substituted $C_2$–$C_6$alkenyl; $C_2$–$C_6$alkynyl; unsubstituted or mono- to tetrahalo-substituted $C_3$–$C_6$cycloalkyl-$C_1$–$C_4$alkyl;

n=0 to 2;

$R_8$=H, $C_1$–$C_4$alkyl, $C_1$–$C_4$haloalkyl, $C_3$–$C_6$cycloalkyl;

X=OR$_5$, SR$_5$, NR$_6$R$_7$, halogen;

$R_6$, $R_7$=independently of one another H, $C_1$–$C_4$alkyl, $C_3$–$C_4$alkenyl, $C_3$–$C_4$alkynyl;

$R_5$=$C_1$–$C_4$alkyl, $C_1$–$C_3$haloalkyl.

2. A compound according to claim 1, wherein $R_8$ is methyl and X is methoxy, $R_2$ is as defined with the exception of halo($C_1$–$C_6$) alkyl and $R_1$, $R_3$, n and W are as defined.

3. A compound according to claim 1, wherein:

$R_1$ is hydrogen, methyl, ethyl or cyclopropyl;

$R_2$ is a phenyl group which carries an unsubstituted or substituted ethynyl group whose possible substituents are: $C_1$–$C_4$alkyl, $C_1$–$C_4$hydroxyalkyl, halogen, $C_1$–$C_4$haloalkyl, cyano, $C_1$–$C_5$alkoxycarbonyl or cyclopropylmethoxycarbonyl; $C_2$–$C_5$alkenyl which is unusbtituted or substituted by alkoxy and/or halogen; N-methyl-N-methoxycarbamoyl; unsubstituted or substituted phenyl, the substituents being selected from the group consisting of $C_1$–$C_4$alkyl, $C_1$–$C_4$alkoxy, CF$_3$, CN, halogen and OCF$_3$; unsubstituted or substituted, five- to six-membered heteroaryl whose substituents can be halogen, cyano, methyl, methoxy, hydroxyl; and $R_3$ is methyl, ethyl or allyl.

4. A compound according to claim 2, wherein $R_1$ is hydrogen, methyl, ethyl or cyclopropyl, $R_2$ is hydrogen, methyl, ethyl, cyclopropyl, cyano, methoxycarbonyl, —S(O)$_n$C$_1$–C$_4$alkyl or C$_1$–C$_5$alkoxy, or is a naphthyl, biphenyl, phenoxyphenyl or phenylthiophenyl ring system each of which can be unsubstituted or substituted by from one to three substituents selected from the group consisting of halogen and C$_1$–C$_2$alkyl;

or is a phenyl radical attached directly or via oxygen, S(O)$_n$ or CH$_2$, which is unsubstituted or is substituted by not more than three substituents selected from the group consisting of C$_1$–C$_4$alkyl, C$_1$–C$_4$alkoxy, halogen, CF$_3$, OCF$_3$, C$_2$–C$_4$alkynyl, NO$_2$, —S(O)$_n$—C$_1$–C$_4$alkyl and a cyclopropylmethoxy group which is unsubstituted or substituted in the ring by one or two halogen atoms;

or is a pyridine or pyrimidine ring which is attached directly or via oxygen or CH$_2$;

or is a thiazoline or oxazoline ring which is unsubstituted or is mono- or disubstituted, identically or differently, by methyl or halogen;

while $R_3$ and n are as defined for formula I.

5. A compound according to claim 4, wherein $R_1$ and $R_3$ are methyl and $R_2$ is methyl, cyano, pyridine or is phenyl attached directly or via oxygen, S(O)$_n$, or CH$_2$, which is unsubstituted or substituted by not more than three substituents selected from the group consisting of methyl, methylthio, methoxy, fluorine, chlorine, bromine, CF$_3$, OCF$_3$, propyn-2-yl, NO$_2$ and cyano; or is a thiazole ring or a naphthyl, biphenyl or phenoxyphenyl ring system which is unsubstituted or is substituted in each case up to twice, identically or differently, by methyl and/or halogen; while A and n are as defined for formula I.

6. A compound according to claim 1, wherein $R_1$, $R_2$ and $R_3$ are methyl.

7. A process for the preparation of a compound of the formula I by reacting an oxime of the formula

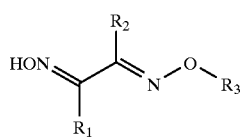

II in which $R_1$, $R_2$ and $R_3$ are as defined for the formula I claim 1, with a benzyl derivative of the general formula

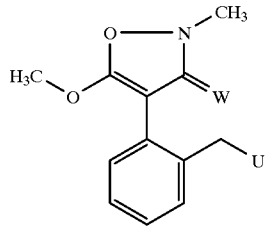

III or, respectively,

-continued

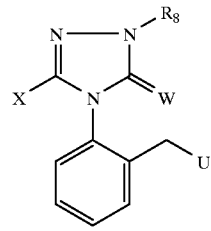

IV in which W is as defined for formula I and U is a leaving group.

8. A process according to claim 7, wherein U is chlorine, bromine, iodine, mesyloxy or tosyloxy and the reaction is carried out in an inert organic diluent in the presence of a base at temperatures between −20° C. and +80° C.

9. A pesticide composition which comprises as active ingredient a compound of the formula I according to claim 1, together with an appropriate carrier materal.

10. A method of controlling and preventing infestation of plants by microorganisms, acarids or insects, which comprises applying as active ingredient a compound of the formula I claim 1, to the plant, to plant parts or to the nutrient medium of the plant.

11. A method according to claim 10, in which the propagation stock is treated.

12. A method according to claim 11, in which seed is treated.

13. A malonic ester derivative of the formula 3

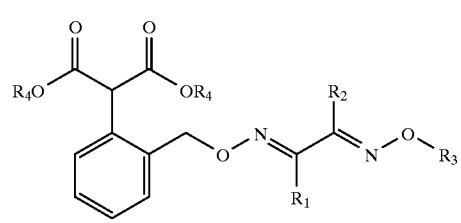

3 in which $R_4$ is methyl or ethyl and $R_1$, $R_2$ and $R_3$ are as defined for formula I claim 1.

14. An isoxazolone derivative of the formula 8

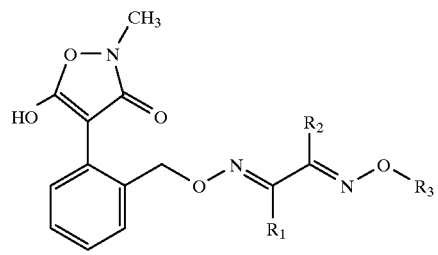

8 in which $R_1$, $R_2$ and $R_3$ are as defined for formula I claim 1.

15. A nitrophenyl derivative of the formula VI

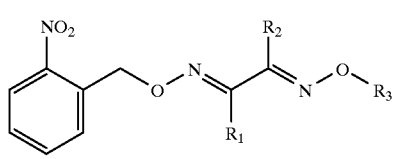

VI in which $R_1$, $R_2$ and $R_3$ are as defined for formula I claim 1.

16. An anilino derivative of the formula 14

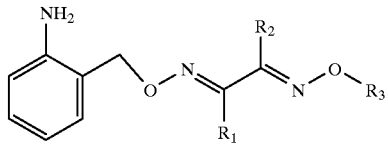

in which $R_1$, $R_2$ and $R_3$ are as defined for formula I claim 1.

17. An iso(thio)cyanate of the formula 17

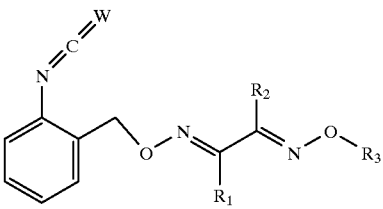

in which W is oxygen or sulfur and in which $R_1$, $R_2$ and $R_3$ are as defined for formula I claim 1.

18. A (thio)guanidine derivative of the formula 19

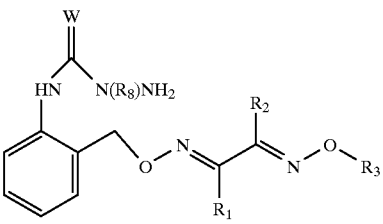

in which W is oxygen or sulfur and in which $R_1$, $R_2$ and $R_3$ are as defined for formula I claim 1.

* * * * *